(12) United States Patent
Kamiya

(10) Patent No.: US 8,465,204 B2
(45) Date of Patent: Jun. 18, 2013

(54) BIOPSY APPARATUS, PHANTOM, SPATIAL RANGE MEASURING APPARATUS, AND SPATIAL RANGE MEASURING METHOD

(75) Inventor: Takeshi Kamiya, Kanagawa-ken (JP)

(73) Assignee: Fujifilm Corporation, Tokyo (JP)

( * ) Notice: Subject to any disclaimer, the term of this patent is extended or adjusted under 35 U.S.C. 154(b) by 106 days.

(21) Appl. No.: 13/317,370

(22) Filed: Oct. 17, 2011

(65) Prior Publication Data
US 2012/0095329 A1    Apr. 19, 2012

(30) Foreign Application Priority Data
Oct. 18, 2010    (JP) ................. 2010-233305

(51) Int. Cl.
*A61B 10/02*    (2006.01)
*A61B 6/00*    (2006.01)

(52) U.S. Cl.
USPC ............. 378/204; 378/37; 378/207; 600/424

(58) Field of Classification Search
USPC ...... 378/18, 37, 204, 207; 250/252.1; 600/424
See application file for complete search history.

(56) References Cited

U.S. PATENT DOCUMENTS

| 5,273,435 | A | 12/1993 | Jacobson | |
|---|---|---|---|---|
| 5,964,715 | A | 10/1999 | Thunberg | |
| 6,241,670 | B1* | 6/2001 | Nambu | 600/427 |
| 6,493,574 | B1* | 12/2002 | Ehnholm et al. | 600/429 |
| 2008/0027354 | A1 | 1/2008 | Gundel | |
| 2008/0187095 | A1* | 8/2008 | Boone et al. | 378/37 |
| 2009/0171244 | A1* | 7/2009 | Ning et al. | 600/567 |
| 2009/0326365 | A1* | 12/2009 | Goldenberg et al. | 600/411 |
| 2011/0201931 | A1* | 8/2011 | Palmeri et al. | 600/440 |
| 2012/0277625 | A1* | 11/2012 | Nakayama | 600/567 |
| 2012/0289824 | A1* | 11/2012 | Nakata | 600/424 |

FOREIGN PATENT DOCUMENTS

| JP | 10-201749 A | 8/1998 |
|---|---|---|
| JP | 2008-029847 A | 2/2008 |
| JP | 2010-075317 A | 4/2010 |

* cited by examiner

*Primary Examiner* — Glen Kao
(74) *Attorney, Agent, or Firm* — Jean C. Edwards, Esq.; Edwards Neils PLLC

(57) ABSTRACT

A biopsy apparatus includes a biopsy needle for insertion into an object to be examined in order to sample tissue of a biopsy region in the object, and a spatial range measuring section, which measures a spatial range within which the biopsy needle is capable of sampling the tissue of the biopsy region, based on an image of a phantom that simulates the object, which is captured after the biopsy needle has been inserted into the phantom and a portion of the phantom has been extracted.

18 Claims, 18 Drawing Sheets

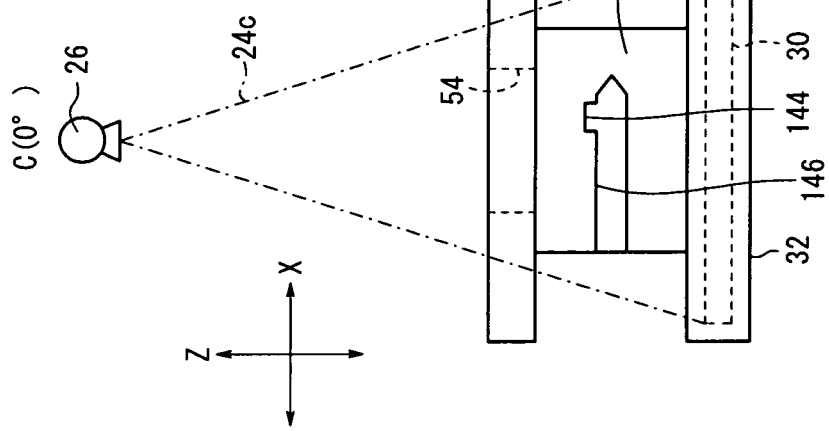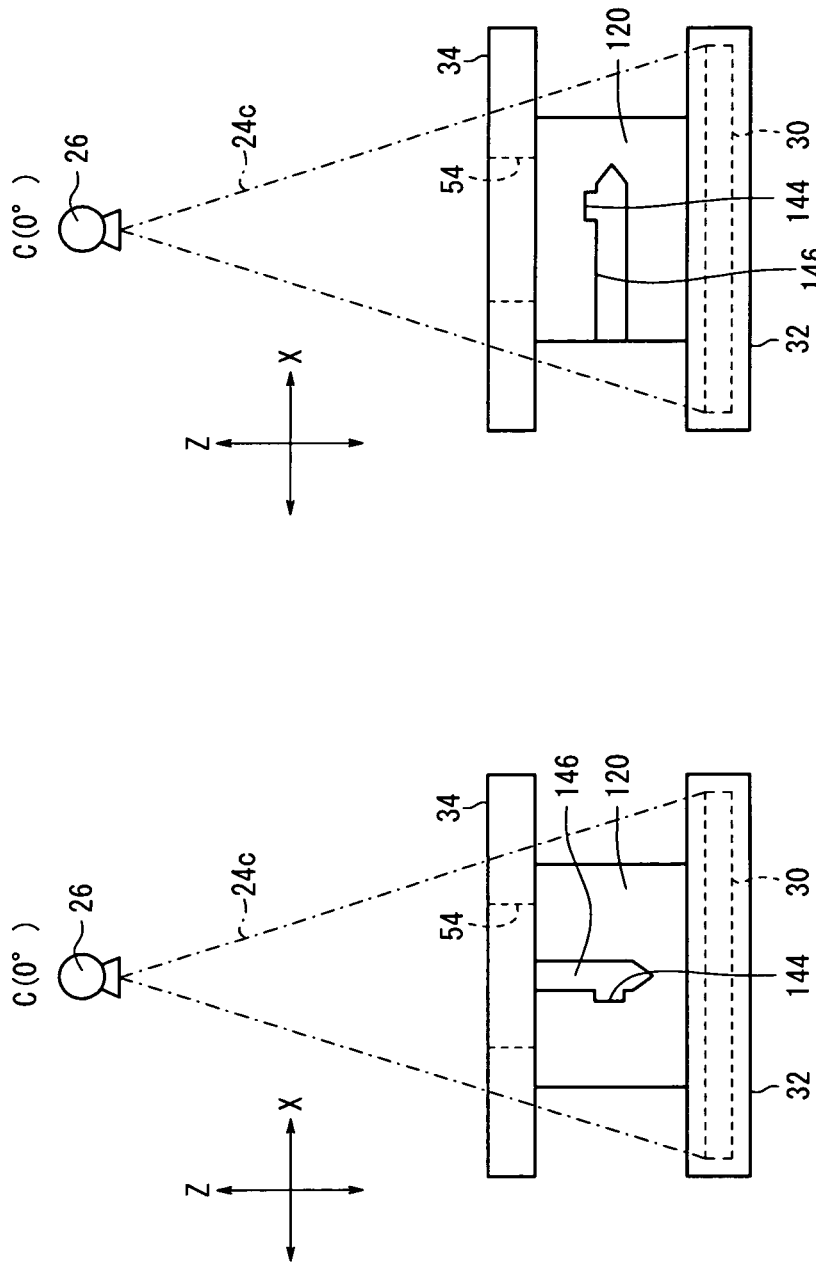

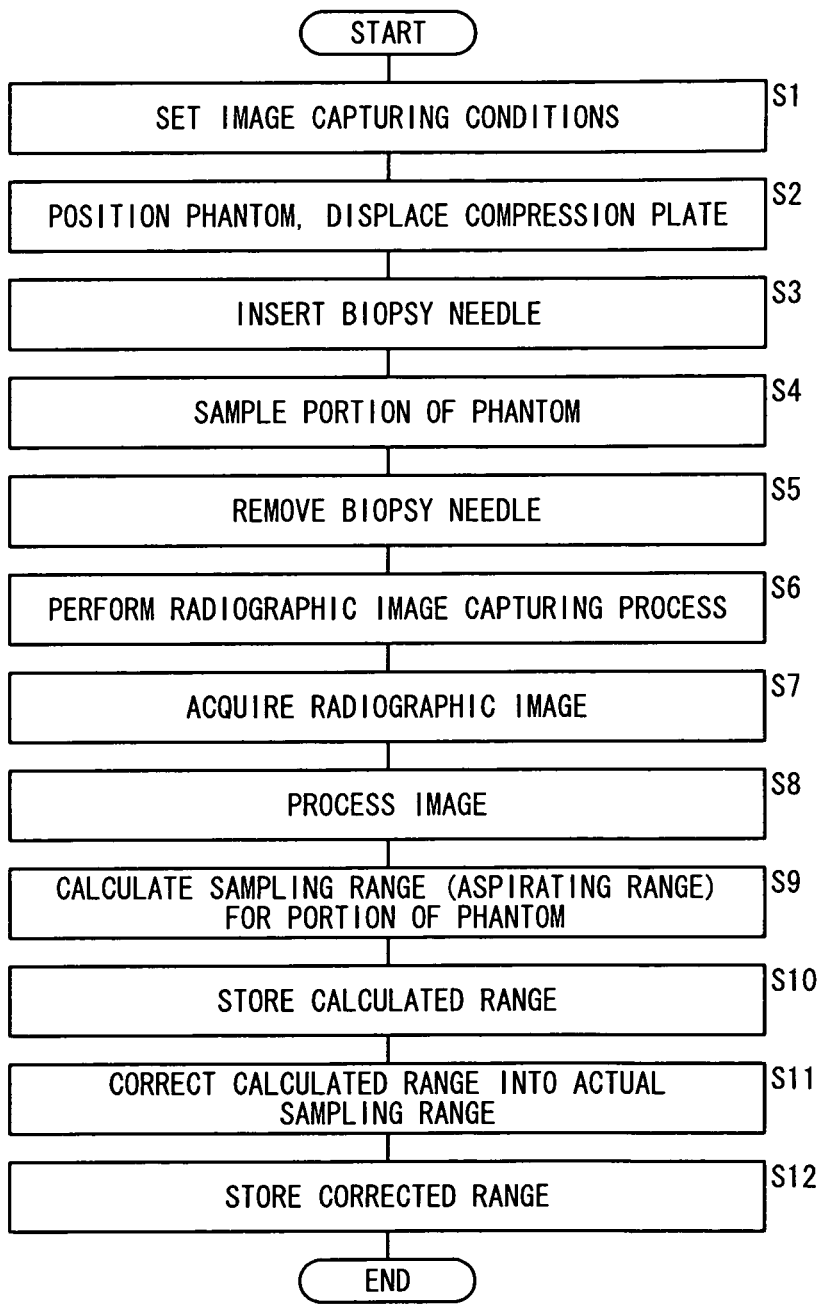

BIOPSY APPARATUS, PHANTOM, SPATIAL RANGE MEASURING APPARATUS, AND SPATIAL RANGE MEASURING METHOD

CROSS-REFERENCE TO RELATED APPLICATION

This application is based upon and claims the benefit of priority from Japanese Patent Application No. 2010-233305 filed on Oct. 18, 2010, of which the contents are incorporated herein by reference.

BACKGROUND OF THE INVENTION

1. Field of the Invention

The present invention relates to a biopsy apparatus for inserting a biopsy needle into an object to be examined in a living body such as a human body or the like, and sampling tissue from a biopsy region in the object to be examined. The present invention also is concerned with a spatial range measuring apparatus and a spatial range measuring method for measuring a spatial range within which the biopsy needle can extract tissue from the biopsy region. The present invention further relates to a phantom for use in training doctors to perform a biopsy procedure, and for measuring a spatial range within which a biopsy needle can sample tissue from a biopsy region.

2. Description of the Related Art

Heretofore, biopsies have been performed in clinical medicine to enable a doctor to sample tissue from a biopsy region in an object to be examined in a living body such as a human body by inserting a biopsy needle into the object to be examined. Generally, it is difficult for the doctor to visually recognize the biopsy region in an object to be examined, such as a lesion in the breast. According to such a biopsy procedure, a stereoscopic image capturing process is carried out on an object to be examined by applying radiation to the object to be examined, thereby acquiring a stereoscopic image of the object to be examined. Then, a three-dimensional coordinate position of a biopsy region in the object to be examined is calculated, and the doctor inserts a biopsy needle into the object to be examined based on the calculated three-dimensional coordinate position. Tissue then is sampled from the biopsy region through the biopsy needle.

According to the biopsy procedure, it is preferable to insert the biopsy needle into the biopsy region without causing significant damage to the living body, and to sample tissue from the biopsy region reliably and accurately, upon undertaking efforts to sample tissue from a biopsy region which is difficult to visually recognize from outside of the living body. Recent years have seen the development of a phantom, which simulates an object to be examined in a human body and tissue of a biopsy region, with a view to improving the skill of doctors who carry out biopsy procedures (see, for example, U.S. Pat. No. 5,273,435).

The phantom disclosed in U.S. Pat. No. 5,273,435 includes a gelatin body in the shape of a compressed human breast, and a plurality of simulated tumors contained within the gelatin body. The simulated tumors are made of a radiopaque material of iodinated oil (black pigment). The gelatin is permeable to X-rays and light. The black pigment is impermeable to light. The phantom is used in the following manner. A trainee, e.g., a doctor, inserts a biopsy needle into the phantom and extracts, as a sample, the black pigment from one of the stimulated tumors along with a portion of the gelatin in the vicinity of the black pigment. Then, the trainee pulls out the biopsy needle in order to remove the sample. In this manner, using the phantom, the trainee is trained to perform a biopsy procedure.

SUMMARY OF THE INVENTION

In an actual biopsy procedure, the doctor is unable to recognize the spatial range within which the doctor can sample tissue from a biopsy region in an object to be examined in a living body such as a human body (patient) using a biopsy needle. At present, it is customary for the doctor to perform biopsies based on the doctor's experience and intuition, without the recognition of such a spatial range. If the doctor inserts the biopsy needle into a region of the object to be examined, which is spaced from the biopsy region, then since the biopsy region is positioned outside of the spatial range covered by the biopsy needle, the biopsy needle is unable to sample tissue from the biopsy region. As a result, the doctor needs to pull out the biopsy needle from the object to be examined, and then reinsert the biopsy needle into the object to be examined. Therefore, the living body suffers an increased physical burden.

The spatial range covered by the biopsy needle may possibly vary depending on various factors such as properties of the biopsy needle. Therefore, the doctor may not perform biopsies satisfactorily if the doctor inserts the biopsy needle into the object to be examined solely based on the experience and intuition of the doctor.

It is an object of the present invention to provide a biopsy apparatus, a phantom, a spatial range measuring apparatus, and a spatial range measuring method, which are capable of measuring, in advance, a spatial range within which a biopsy needle can sample tissue from a biopsy region.

To achieve the above object, there is provided in accordance with the present invention a biopsy apparatus comprising a biopsy needle for insertion into an object to be examined in a living body thereby to sample tissue of a biopsy region in the object, and a spatial range measuring section, which measures a spatial range within which the biopsy needle is capable of sampling the tissue of the biopsy region, based on an image of a phantom that simulates the object, the image being captured after the biopsy needle has been inserted into the phantom and a portion of the phantom has been extracted.

According to the present invention, there also is provided a spatial range measuring apparatus comprising a spatial range measuring section for measuring a spatial range within which a biopsy needle is capable of sampling tissue of a biopsy region in an object to be examined in a living body, based on an image of a phantom that simulates the object, the image being captured after the biopsy needle has been inserted into the phantom and a portion of the phantom has been extracted.

According to the present invention, there also is provided a spatial range measuring method comprising inserting a biopsy needle into a phantom that simulates an object to be examined in a living body and extracting a portion of the phantom, acquiring an image of the phantom after the portion of the phantom has been extracted, and measuring a spatial range within which the biopsy needle is capable of sampling tissue of a biopsy region in the object, based on the image of the phantom.

A spatial range within which the biopsy needle is capable of sampling tissue of the biopsy region in the object is measured based on the image of the phantom, which is captured after the biopsy needle has been inserted into the phantom and a portion of the phantom has been extracted. Therefore, a spatial range within which the biopsy needle is capable of sampling tissue of the biopsy region can be measured in advance, before a biopsy procedure for inserting the biopsy needle into the object to be examined and sampling tissue of the biopsy region is performed.

Accordingly, a doctor who handles the biopsy apparatus can avoid inserting the biopsy needle into the object at a location spaced from the biopsy region. Even if the spatial range is changed due to factors such as properties of the biopsy needle, the biopsy procedure is performed according to the spatial range that is measured, and hence the biopsy procedure is prevented from failing due to a change in the spatial range.

Since the phantom and the living body have different properties, the spatial range within which the phantom can be sampled by the biopsy needle and the spatial range within which the object can be sampled by the biopsy needle may differ from each other.

The spatial range measuring section measures a first spatial range depending on the portion of the phantom and which is formed in the phantom by extracting the portion of the phantom, based on the image of the phantom, and corrects the measured first spatial range into a second spatial range within which the biopsy needle is capable of sampling the tissue of the biopsy region.

Since the spatial range measuring section determines the second spatial range within which the biopsy needle can sample tissue of the biopsy region in an actual biopsy procedure, the doctor can reliably extract the tissue of the biopsy region by inserting the biopsy needle into the object in order to locate the biopsy region within the second spatial range.

The spatial range measuring section corrects the measured first spatial range into the second spatial range using corrective data based on properties of the phantom and properties of the object. The second spatial range can thus be determined accurately.

The corrective data may comprise either data based on a spatial range within which the biopsy needle is capable of sampling the portion of the phantom and the spatial range within which the biopsy needle is capable of sampling the tissue of the biopsy region, or data based on characteristic values of a material that makes up the phantom and characteristic values of a material that makes up the object. The second spatial range can thus be determined accurately by correcting the first spatial range into the second spatial range using the above data.

The data based on the spatial ranges represent spatial ranges formed in the phantom and the object after the portion of the phantom and the tissue of the object are extracted by the biopsy needle, which is inserted in the phantom and the object. The data based on the characteristic values represent a modulus of elasticity of the material that makes up the phantom and a modulus of elasticity of the material that makes up the object. The spatial range measuring section can determine the second spatial range by identifying the first spatial range from a contrast ratio between the first spatial range and the material around the first spatial range in the image of the phantom, and by comparing the identified first spatial range and the measured spatial range. Alternatively, the spatial range measuring section can determine the second spatial range by multiplying the data representative of the identified first spatial range by a corrective coefficient based on each of the aforementioned moduli of elasticity.

The spatial range measuring section may calculate the second spatial range when the image of the phantom is acquired, or immediately before a biopsy procedure is carried out. To calculate the second spatial range in this manner, the biopsy apparatus should preferably further include a first spatial range storage section that stores the first spatial range measured by the spatial range measuring section, a corrective data storage section that stores the corrective data, and a second spatial range storage section that stores the second spatial range corrected by the spatial range measuring section. With this arrangement, the spatial range measuring section can measure the first spatial range, and correct the first spatial range into the second spatial range at a suitable time, immediately after the image of the phantom has been acquired or immediately before the doctor performs a biopsy procedure.

As described above, the spatial range (second spatial range) within which the biopsy needle is capable of sampling tissue of the biopsy region may possibly become changed due to factors such as properties of the biopsy needle.

To solve this problem, the biopsy apparatus should preferably further include a biopsy region indicator that indicates the biopsy region to be sampled by the biopsy needle, a biopsy region position calculator that calculates the position of the biopsy region indicated by the biopsy region indicator, a changing factor data storage section that stores changing factor data representative of a changing factor of the second spatial range, and a decision section that reads the second spatial range from the second spatial range storage section, reads the changing factor data from the changing factor data storage section, and determines whether the biopsy needle is capable of sampling the tissue of the biopsy region indicated by the biopsy region indicator, based on the position of the biopsy region, the read second spatial range, and the read changing factor data.

In a case where the doctor operates the biopsy region indicator in order to indicate the biopsy region, and the biopsy region position calculator calculates the position of the biopsy region, the decision section determines whether or not the biopsy needle is capable of sampling tissue from the biopsy region based on the position of the biopsy region, the second spatial range, and the changing factor data. Inasmuch as the decision section determines whether or not the biopsy needle is capable of sampling tissue from the biopsy region in view of changing factors of the second spatial range, if the result is affirmative, thus indicating that the biopsy needle is capable of sampling tissue from the biopsy region, then a biopsy procedure can be performed. On the other hand, if the result is negative, thus indicating that the biopsy needle is incapable of sampling tissue from the biopsy region, then the biopsy needle can be prevented from being erroneously inserted into the object.

If the decision of the decision section is annunciated, i.e., indicated outwardly, through an annunciating section, then the doctor can easily recognize whether or not a biopsy procedure should be carried out or not.

The biopsy apparatus should preferably further include a biopsy needle position calculator that calculates the position of the biopsy needle in a case that the biopsy region indicator indicates the biopsy region, and a biopsy needle movement distance calculator that calculates a distance that the biopsy needle moves with respect to the biopsy region, based on the position of the biopsy region and the position of the biopsy needle.

If the decision section judges that the biopsy needle is capable of sampling the tissue of the biopsy region, then the decision section indicates outwardly through the annunciating section that the biopsy needle is capable of sampling the tissue of the biopsy region, and permits the biopsy needle movement distance calculator to calculate the distance that the biopsy needle moves, and also permits the annunciating section to indicate the calculated distance.

Further, if the decision section judges that the biopsy needle is incapable of sampling the tissue of the biopsy region, then the decision section indicates outwardly through the annunciating section a prohibition of sampling the tissue of the biopsy region by the biopsy needle, and prohibits the biopsy needle movement distance calculator from calculating the distance that the biopsy needle moves.

If the decision section makes an affirmative decision thus indicating that the biopsy needle is capable of sampling tissue from the biopsy region, then since the affirmative decision and the distance that the biopsy needle moves are indicated by the annunciating section, the doctor is notified of the affirmative decision and the distance. Thus, the doctor can accurately and reliably perform a biopsy procedure according to the affirmative decision and the distance, which are displayed. Since the biopsy needle movement distance calculator calculates the distance that the biopsy needle moves according to the affirmative result, if the biopsy needle is moved by the calculated distance, the tissue of the biopsy region, which is indicated by the biopsy region indicator, reliably falls within the second spatial range. As a result, the tissue of the biopsy region can efficiently be extracted.

If the decision section makes a negative decision thus indicating that the biopsy needle is incapable of sampling tissue from the biopsy region, then since only the negative decision is indicated by the annunciating section, thereby letting the doctor know the negative decision, the doctor can easily recognize that a biopsy procedure cannot be performed.

If the second spatial range is changed (reduced) due to factors such as the properties of the biopsy needle, the tissue of the biopsy region may fall outside of the second spatial range and may not be extracted, even if the biopsy needle is accurately inserted into the breast.

The decision section may judge that the biopsy needle is incapable of sampling the tissue of the biopsy region if the second spatial range is smaller than a threshold value based on the changing factor data. A biopsy procedure is thus reliably canceled if there is a possibility that a biopsy procedure will fail due to a change in the second spatial range.

Also, in a case where an insertable range within which the biopsy needle can be inserted into the object is set in advance, the decision section may judge that the biopsy needle is incapable of sampling the tissue of the biopsy region if the position of the biopsy region falls outside of the insertable range within which the biopsy needle can be inserted into the object. Since there is a possibility that the biopsy procedure will fail if the position of the biopsy region falls outside of the insertable range, the biopsy procedure is reliably canceled by making such a decision.

The biopsy apparatus may further include a biopsy needle movement controller that controls movement of the biopsy needle. If the decision section permits the biopsy needle movement distance calculator to calculate the distance that the biopsy needle moves, the biopsy needle movement distance calculator calculates the distance that the biopsy needle moves and outputs the calculated distance to the biopsy needle movement controller, and the biopsy needle movement controller inserts the biopsy needle into the object based on the distance input thereto. The biopsy apparatus then moves the biopsy needle based on the calculated distance, thereby automatically performing a biopsy procedure on the object. As a result, the burden posed on the doctor by the biopsy procedure can be reduced.

The biopsy needle may have a sampler defined in a side wall near a tip end thereof, for aspirating and extracting the tissue of the biopsy region or the portion of the phantom. The sampler may be connected through an aspirating passage to an aspirating device for aspirating the tissue of the biopsy region or the portion of the phantom. The changing factor data may comprise data representing characteristics of the biopsy needle including the sampler, characteristics of the aspirating passage, and characteristics of the aspirating device. The decision section can thus determine more accurately whether or not the biopsy needle is capable of sampling tissue from the biopsy region.

The image of the phantom may be captured by applying radiation from a radiation source to the phantom after the portion of the phantom has been extracted, and converting the radiation that has passed through the phantom into a radiographic image with a radiation detector.

If the biopsy region is spaced from the sampler along the direction in which the biopsy needle is inserted into the object, moving the biopsy needle along that direction so as to displace the sampler toward the position of the biopsy region brings the tissue of the biopsy region into the second spatial range, thereby making it possible to extract tissue from the biopsy region.

If the biopsy region is spaced from the sampler along the direction in which the biopsy needle is inserted into the breast and falls outside of the second spatial range, then it becomes more difficult to move the biopsy needle radially to bring the biopsy region into the second spatial range. In such a case, it is necessary to pull out the biopsy needle from the object and reinsert the biopsy needle into the object.

To avoid such a difficulty, it is preferable for the radiation source to apply radiation at least along the direction in which the biopsy needle is inserted into the phantom, and for the radiation detector to convert radiation that has passed through the phantom into a radiographic image on a projection plane of the radiation, which is substantially perpendicular to the direction in which the biopsy needle has been inserted into the phantom.

In this manner, the radiographic image becomes an image on a plane (projection plane) along a radial direction of the biopsy needle, i.e., along a direction perpendicular to the direction in which the biopsy needle is inserted into the phantom. By determining the width of the second spatial range along the radial direction, it is possible to determine easily whether or not the biopsy region falls within the second spatial range before the biopsy procedure actually is performed.

The biopsy needle may be inserted into the phantom a plurality of times and may extract respective portions of the phantom, thereby forming a plurality of sampling spaces in the phantom depending on the portions of the phantom. The sampling spaces may be formed so as not to overlap each other in side elevation.

With the sampling spaces being formed in the phantom, it is easy to determine second spatial ranges at respective positions in the object that correspond to the sampling spaces. If a plurality of biopsy needles having different characteristics are inserted into the phantom so as to form a plurality of sampling spaces therein, then the second spatial ranges, which depend on those sampling spaces, may possibly differ from each other. In such a case, second spatial ranges, which depend on the respective biopsy needles, may be determined in advance, and in a case where a biopsy procedure is carried out, one of the biopsy needles may be selected depending on the position and size of the biopsy region. In this manner, the biopsy procedure can be carried out reliably and efficiently.

The phantom simulates the breast of a human body, and the biopsy needle may be inserted into the phantom a plurality of times in spaced relation to the chest wall of the human body, thereby forming the sampling spaces in the phantom. Also in this case, the second spatial range in the breast depending on the respective sampling spaces can be determined easily.

The phantom should preferably include a first member that simulates an object to be examined in a living body, and a second member disposed in the first member and that simulates a tissue of a biopsy region in the object. The first member is made of a material permeable to radiation, the second member is made of a material less permeable to radiation than the first member, or is made of a material impermeable to radiation. A spatial range within which a biopsy needle is capable of sampling the tissue of the biopsy region is measured based on an image of the phantom, which is captured after the biopsy needle has been inserted into the phantom and a portion of the phantom has been extracted.

Since the second member, which simulates tissue of the biopsy region, is disposed in the first member, it is possible to train a doctor to perform a biopsy procedure for sampling tissue. The doctor is trained to perform a biopsy procedure using the phantom, whereby the doctor becomes more skillful in performing the biopsy procedure, for sampling calcified tissue in the breast, for example. Since the second member is less permeable to radiation than the first member or is impermeable to radiation, in a case where a radiographic image capturing process is performed on the phantom to acquire a radiographic image thereof, it is possible to easily distinguish the first member from the second member. By measuring a spatial range within which the biopsy needle can extract tissue of the biopsy region based on an image of the phantom, the aforementioned advantages of the biopsy apparatus, the spatial range measuring apparatus, and the spatial range measuring method can easily be achieved.

If the second member comprises a plurality of second members in the form of particles, which are disposed substantially uniformly throughout the interior of the first member, then it is possible to train the doctor to accurately position the biopsy needle in the tissue of the biopsy region.

The above and other objects, features, and advantages of the present invention will become more apparent from the following description when taken in conjunction with the accompanying drawings, in which a preferred embodiment of the present invention is shown by way of illustrative example.

BRIEF DESCRIPTION OF THE DRAWINGS

FIGS. 11A and 11B are schematic views illustrative of radiographic image capturing processes performed on the phantom and the receptacle from which the biopsy needle has been pulled out;

FIG. 15 is a flowchart of a sequence for measuring a spatial range using the biopsy apparatus and the mammographic system shown in FIGS. 1, 2 and 4;

DESCRIPTION OF THE PREFERRED EMBODIMENTS

A biopsy apparatus according to a preferred embodiment of the present invention in relation to a phantom, a spatial range measuring apparatus, and a spatial range measuring method will be described below with reference to FIGS. 1 through 18C of the accompanying drawings.

Figure 1:
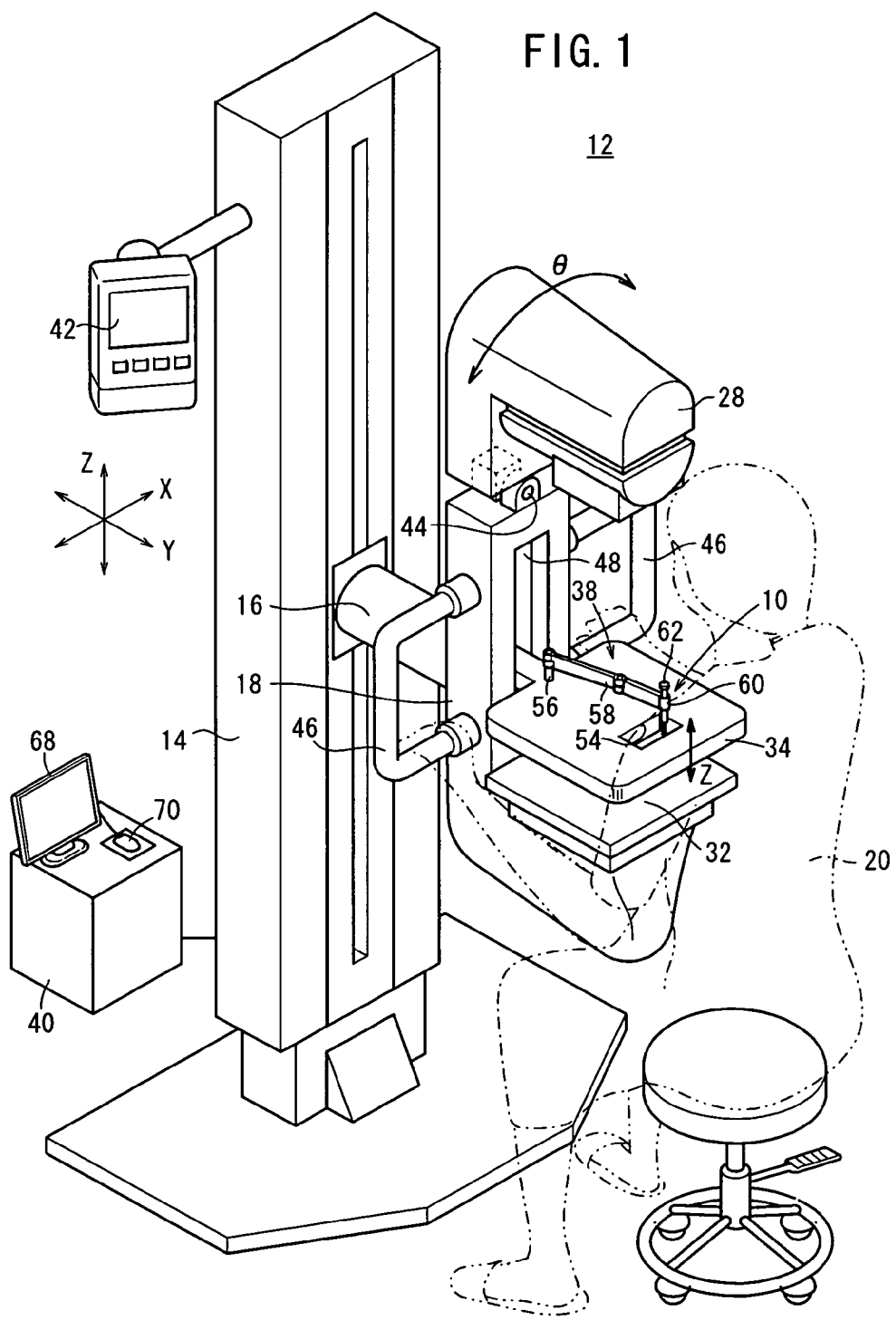
FIG. 1 is a perspective view of a mammographic system incorporating a biopsy apparatus therein according to an embodiment of the present invention.
Figure 2:
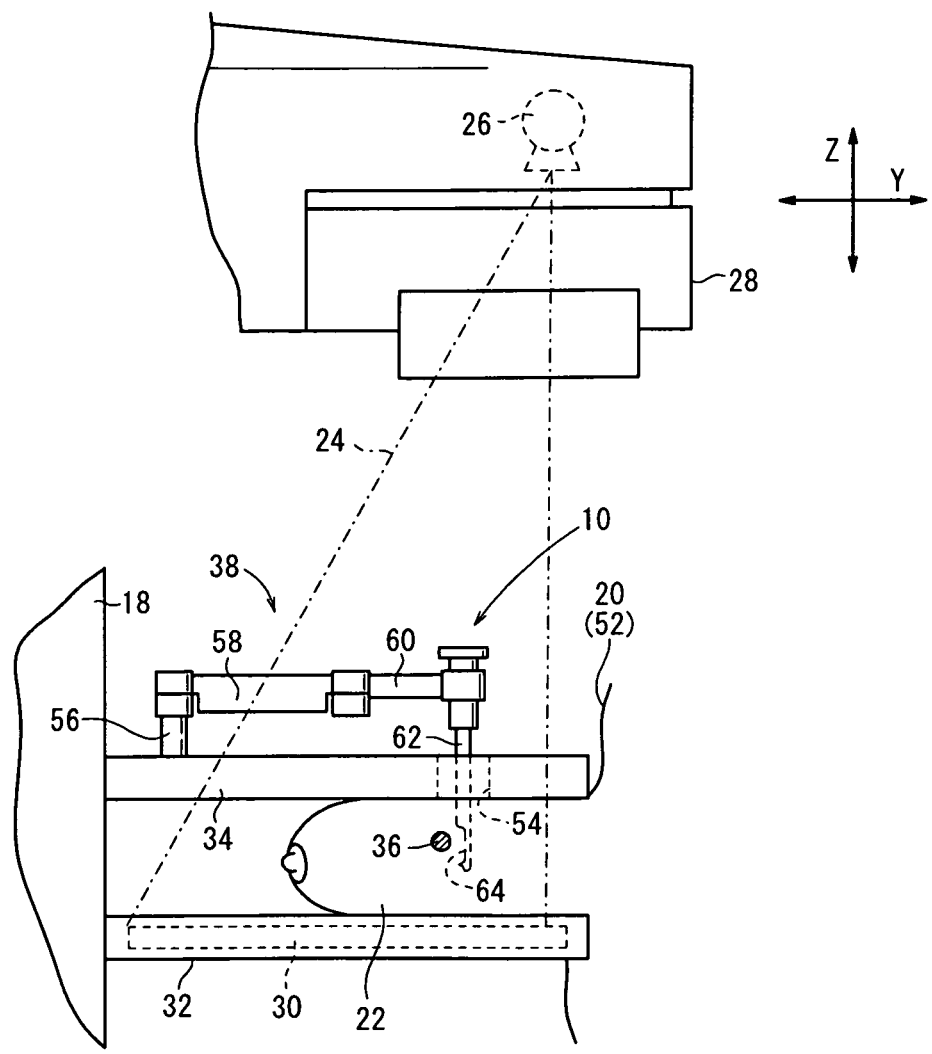
FIG. 2 is an enlarged fragmentary side elevational view of the mammographic system shown in FIG. 1.

Basic Arrangement of the Embodiment:

As shown in FIGS. 1 and 2, a biopsy apparatus 10 according to the present embodiment is incorporated in a mammographic system 12.

The mammographic system 12 basically includes an upstanding base 14, a vertical arm 18 fixed to a distal end of a swing shaft 16 disposed substantially centrally on the base 14, a radiation source housing unit 28 fixed to an upper end of the arm 18 and housing therein a radiation source 26 for applying radiation 24 to a breast 22 as an object to be examined of an examinee (human body, living body) 20, an image capturing base 32 mounted on a lower end of the arm 18 and housing therein a solid-state detector (radiation detector) 30 for detecting radiation 24 that has passed through the breast 22, a compression plate 34 for compressing and holding the breast 22 against the image capturing base 32, a biopsy hand assembly 38 mounted on the compression plate 34 for sampling tissue from a biopsy region 36 of the breast 22, and a console (spatial range measuring apparatus) 40 electrically connected to the base 14 through a wired link.

In FIGS. 1 and 2, the mammographic system 12 applies radiation 24 to the breast 22 of the examinee 20 and samples tissue from the biopsy region 36 while the breast 22 of the examinee 20, who is in a sitting position, is compressed and secured by the compression plate 34 and the image capturing base 32. To the base 14, there is connected a display control panel (annunciating section) 42 for setting and displaying image capturing conditions representing an image capturing region, etc., of the examinee 20, ID information of the examinee 20, etc.

The arm 18, to which the radiation source housing unit 28 and the image capturing base 32 are secured, is angularly moved about the swing shaft 16, whereby the direction of the radiation source housing unit 28 and the image capturing base 32 with respect to the breast 22 of the examinee 20 is adjusted. The radiation source housing unit 28 is operatively coupled to the arm 18 by a hinge 44, and can be turned about the hinge 44 in the directions indicated by the arrow θ independently of the image capturing base 32. Handles 46, which are gripped by the examinee 20, are mounted on respective sides of the arm 18 and face away from each other along directions indicated by the arrow X.

The compression plate 34 has a proximal end inserted in a groove 48 defined in the arm 18. The compression plate 34 is disposed between the radiation source housing unit 28 and the image capturing base 32. The compression plate 34 is vertically displaceable in the directions indicated by the arrow Z. A distance d (see FIG. 3) by which the compression plate 34 is displaced can be detected by a displacement distance detector 50 (see FIG. 4).

The biopsy hand assembly 38 is mounted on a surface of the compression plate 34, which faces toward the radiation source 26, in the vicinity of the groove 48. The compression plate 34 has an opening 54 defined therein near a chest wall 52 (see FIG. 2) of the examinee 20, for allowing the biopsy hand assembly 38 to remove a tissue sample from the biopsy region 36 of the breast 22. The compression plate 34 is detachable from the groove 48. A plurality of compression plates 34 with differently shaped openings 54 defined therein may be kept available for ready use. One of the compression plates 34, the opening 54 of which is best suited to the examinee 20, may be used to let the examinee 20 sit in a natural stress-free position while a biopsy procedure is carried out on the examinee 20.

The biopsy hand assembly 38 comprises a post 56 fixedly mounted on the compression plate 34, a first arm 58 having an end pivotally supported on the post 56 and angularly movable about the post 56 along the surface of the compression plate 34, and a second arm 60 having an end pivotally supported on the other end of the first arm 58 and angularly movable about the other end of the first arm 58 along the surface of the compression plate 34. A biopsy needle 62, which is movable in the directions indicated by the arrow Z, is mounted on the other end of the second arm 60.

The biopsy needle 62 includes a sampler 64 for aspirating and sampling tissue, e.g., calcified tissue, from the biopsy region 36 of the breast 22. The sampler 64 can be positioned in the vicinity of the biopsy region 36 by moving the first arm 58 and the second arm 60 of the biopsy hand assembly 38 in an X-Y plane along the surface of the compression plate 34, and also by moving the biopsy needle 62 in the directions indicated by the arrow Z. The biopsy needle 62 may be moved in the directions indicated by the arrow Z, i.e., lifted and lowered, automatically by the biopsy hand assembly 38 or manually by a doctor who operates the mammographic system 12.

Figure 3:
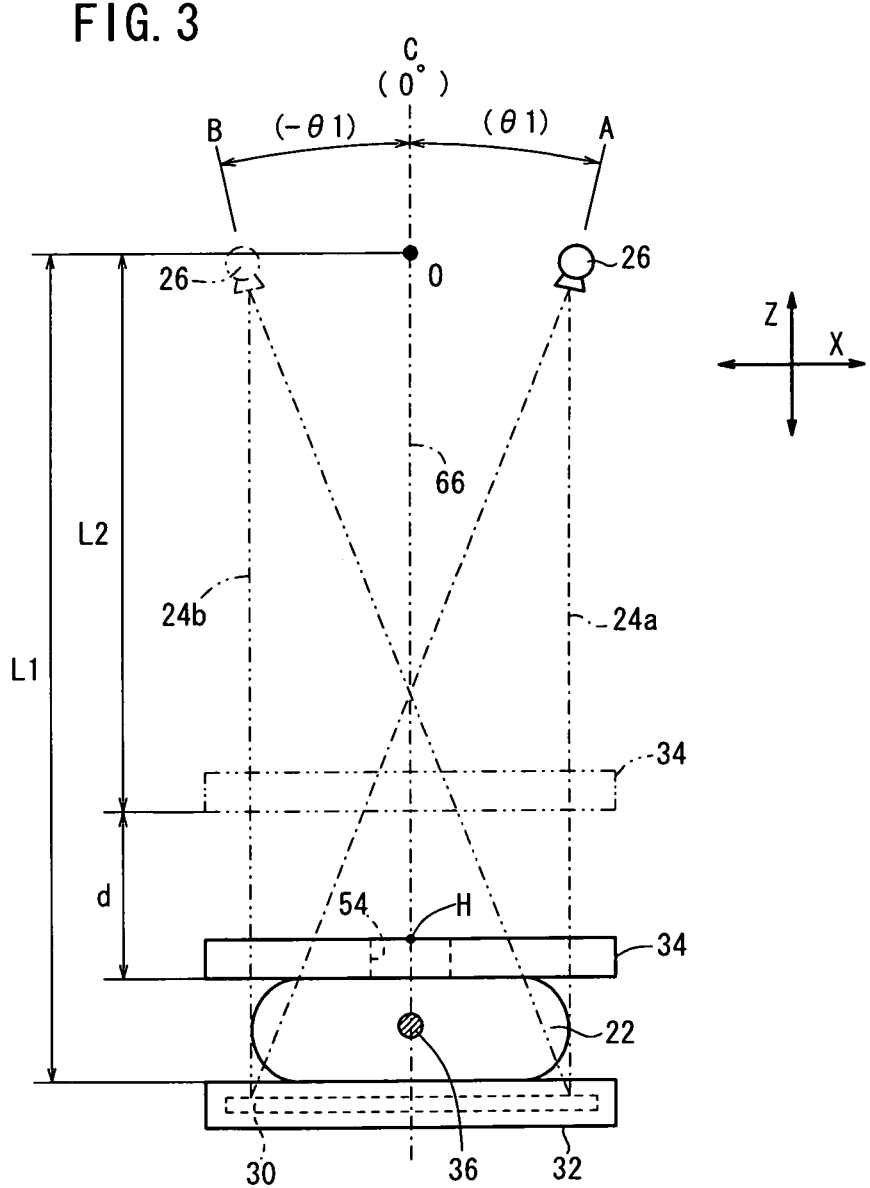
FIG. 3 is a schematic view illustrative of a stereoscopic image capturing process for capturing a stereoscopic image of a breast.

As shown in FIG. 3, the mammographic system 12 performs a stereoscopic image capturing process by applying radiation 24a, 24b to the breast 22 from the radiation source 26, which is disposed in positions A and B obliquely to a vertical axis (central axis) 66 of the solid-state detector 30. The solid-state detector 30 detects radiation 24a, 24b that has passed through the breast 22, and converts the detected radiation 24a, 24b into respective radiographic images (stereoscopic image).

In the mammographic system 12, the number of stereoscopic images that are captured and the order in which such images are captured are set as desired by the doctor or the like. The radiation source 26 is moved angularly between the positions A and B by turning the radiation source housing unit 28 about the hinge 44.

In the stereoscopic image capturing process according to the present embodiment, the radiation source 26 applies radiation 24a, 24b from the respective positions A and B in a condition where the radiation source 26 is in the positions A and B. However, the mammographic system 12 may perform another stereoscopic image capturing process, in which the radiation source 26 applies radiation 24a, 24b from the position A and another position C on the vertical axis 66 in a condition where the radiation source 26 is in the positions A and C. Still another stereoscopic image capturing process may be performed, in which the radiation source 26 applies radiation 24a, 24b from the respective positions B and C in a condition where the radiation source 26 is in the positions B and C.

Figure 4:
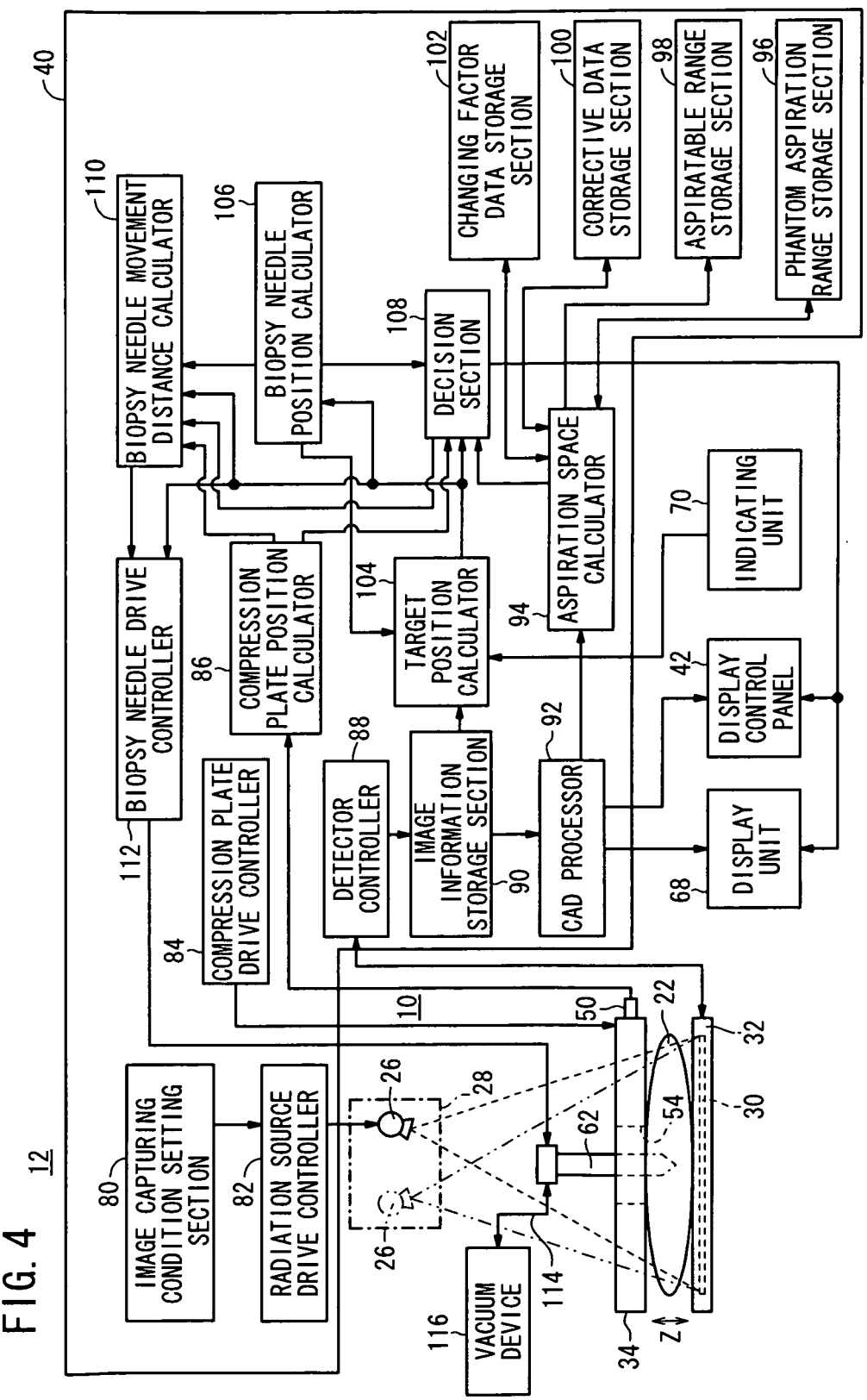
FIG. 4 is a block diagram of the mammographic system including the biopsy apparatus shown in FIG. 1.

As shown in FIGS. 1 and 4, the console 40 is electrically connected to a display unit (annunciating section) 68 and an indicating unit (biopsy region indicator) 70. The display unit 68 displays two radiographic images (stereoscopic images), which are acquired in respective stereoscopic image capturing processes. The indicating unit 70 is a pointing device such as a mouse or the like. In a case where the doctor sees details (a stereoscopic image) displayed on the display unit 68, the doctor can indicate a lesion (target, biopsy region 36) from which tissue is to be sampled, among a plurality of lesions in the stereoscopic image, using the pointing device. If the display unit 68 is in the form of a touch panel, then the display unit 68 and the indicating unit 70 may be combined integrally with each other.

Rather than the two individual radiographic images, the display unit 68 may display a three-dimensional radiographic image generated from the two radiographic images. If the display unit 68 displays a three-dimensional radiographic image, then the display unit 68 also displays three-dimensional images of the lesions. If the indicating unit 70 is a three-dimensional pointing device such as a three-dimensional mouse or the like, then using the indicating unit 70, the doctor can easily indicate a lesion to be sampled from among the displayed three-dimensional images of the lesions.

The console 40 further includes an image capturing condition setting section 80, a radiation source drive controller 82, a compression plate drive controller 84, a detector controller 88, an image information storage section 90, and a CAD (computer aided diagnosis) processor 92, as components involved in the stereoscopic image capturing process.

The image capturing condition setting section 80 sets image capturing conditions, including a tube current and a tube voltage of the radiation source 26, irradiation dosages and irradiation times of the radiation 24 (24a, 24b), an image capturing method, and an imaging sequence. The image capturing condition setting section 80 may also set, as image capturing conditions, imaging angles (angles at the positions A, B and C) in the stereoscopic image capturing processes, and positional data including positional data of the image capturing base 32, initial positional data of the compression plate 34, and positional data of the opening 54.

The positional data of the image capturing base 32 represent a distance L1 in a three-dimensional coordinate system from the origin (reference point) 0 shown in FIG. 3 to an upper surface of the image capturing base 32 that contacts the breast 22, i.e., which faces the compression plate 34, along the directions indicated by the arrow Z. The initial positional data of the compression plate 34 represent a distance L2 from the origin O to a lower surface of the compression plate 34 that contacts the breast 22, i.e., which faces the image capturing base 32, along the directions indicated by the arrow Z, in a case where the compression plate 34 is in an initial state. In the present embodiment, the origin O, which may be set in any desired position, is set on the vertical axis 66. The initial state of the compression plate 34 refers to a state prior to compressing the breast 22. In a case where the compression plate 34 is in the initial state, the compression plate 34 is in the position indicated by the two-dot-and-dash lines shown in FIG. 3. The positional data of the opening 54 represent three-dimensional coordinate positions, with respect to the origin O, of points of intersection of the four line segments, which define an open end of the opening 54 in the lower surface of the compression plate 34.

The compression plate drive controller 84 serves to move the compression plate 34 in the directions indicated by the arrow Z. The radiation source drive controller 82 serves to energize the radiation source 26 according to the image capturing conditions under a condition in which the breast 22 is compressed and held in position by the compression plate 34 and the image capturing base 32. The detector controller 88 controls the solid-state detector 30 to store radiographic images, which are converted from the radiation 24 (24a, 24b) by the solid-state detector 30, in the image information storage section 90. In a radiographic image capturing process performed on the breast 22, the detector controller 88 stores in the image information storage section 90 two radiographic images (stereoscopic image), which are captured respectively at two image capturing angles (stereoscopic angles).

The CAD processor 92 processes the radiographic images stored in the image information storage section 90, and displays the processed radiographic images (stereoscopic images) on the display unit 68 and/or the display control panel 42. The CAD processor 92 may also perform an image processing sequence so as to display the two radiographic images as respective two-dimensional images on the display unit 68 and/or the display control panel 42. Alternatively, the CAD processor 92 may generate a three-dimensional radiographic image from two two-dimensional images, and may display the generated three-dimensional radiographic image on the display unit 68 and/or the display control panel 42.

As components that are involved in the biopsy procedure, the console 40 further includes a compression plate position calculator 86, an aspiration space calculator (spatial range measuring section) 94, a phantom aspiration range storage section (first spatial range storage section) 96, an aspiratable range storage section (second spatial range storage section) 98, a corrective data storage section 100, a changing factor data storage section 102, a target position calculator (biopsy region position calculator) 104, a biopsy needle position calculator 106, a decision section 108, a biopsy needle movement distance calculator 110, and a biopsy needle drive controller (biopsy needle movement controller) 112.

The biopsy apparatus 10 according to the present embodiment is made up of the above components of the console 40, which are involved in biopsy procedures, the biopsy hand assembly 38, the display control panel 42, the opening 54, the biopsy needle 62, the display unit 68, and the indicating unit 70.

Of the above components of the console 40, which make up part of the biopsy apparatus 10, basic details of certain components, which are directly related to the insertion of the biopsy needle 62 into the breast 22, will be described below.

The compression plate position calculator 86 calculates the position of the lower surface of the compression plate 34 with respect to the origin O along the directions indicated by the arrow Z, based on the initial positional data of the compression plate 34 and an output signal from the displacement distance detector 50.

The target position calculator 104 calculates the three-dimensional coordinate position (hereinafter referred to as a "target coordinate position") of the biopsy region 36 indicated by the indicating unit 70, and outputs information of the target coordinate position to the decision section 108 and the biopsy needle movement distance calculator 110. The biopsy needle position calculator 106 calculates the three-dimensional coordinate position of the biopsy needle 62, which is displayed in a stereoscopic image of the breast 22, and outputs information of the calculated three-dimensional coordinate position to the decision section 108 and the biopsy needle movement distance calculator 110. The target coordinate position and the three-dimensional coordinate position of the biopsy needle 62 are calculated according to known principles used in calculating three-dimensional coordinate positions for stereoscopic image capturing processes.

The decision section 108 basically determines whether or not the biopsy needle 62 is capable of sampling tissue from the biopsy region 36 based on the target coordinate position, the three-dimensional coordinate position of the biopsy needle 62, the position of the lower surface of the compression plate 34 in the directions indicated by the arrow Z, and the positional data of the opening 54. Details of the determining process carried out by the decision section 108 will be described later.

If the decision section 108 judges that the biopsy needle 62 is capable of sampling tissue from the biopsy region 36, then the decision section 108 displays an affirmative decision, i.e., a decision indicating that the biopsy needle 62 is capable of sampling tissue from the biopsy region 36, or in other words, a decision to permit the biopsy procedure, on the display unit 68 and/or the display control panel 42, in order to enable the doctor to see the affirmative decision. The decision section 108 also permits the biopsy needle movement distance calculator 110 to calculate a distance that the biopsy needle 62 moves, and to output the calculated distance to the display unit 68 and/or the display control panel 42. If the decision section 108 judges that the biopsy needle 62 is not capable of sampling tissue from the biopsy region 36, then the decision section 108 displays a negative decision, i.e. a decision indicating that the biopsy needle 62 is not capable of sampling tissue from the biopsy region 36, or in other words, a decision to prohibit the biopsy procedure, on the display unit 68 and/or the display control panel 42, in order to enable the doctor to see the negative decision, and further instructs the biopsy needle movement distance calculator 110 not to calculate the distance that the biopsy needle 62 moves.

If the biopsy needle movement distance calculator 110 receives information from the decision section 108, which indicates permission to calculate the distance that the biopsy needle 62 moves and permission to output the calculated distance to the display unit 68 and/or the display control panel 42, then the biopsy needle movement distance calculator 110 calculates the distance that the biopsy needle 62 moves with respect to the biopsy region 36, i.e., the distance between the present position of the biopsy needle 62 and the position thereof where the sampler 64 can extract tissue from the biopsy region 36, based on the target coordinate position, the three-dimensional coordinate position of the biopsy needle 62, the position of the lower surface of the compression plate 34 in the directions indicated by the arrow Z, and the positional data of the opening 54. Then, the biopsy needle movement distance calculator 110 outputs the calculated distance to the biopsy needle drive controller 112 and the display unit 68 and/or the display control panel 42. Therefore, the display unit 68 and/or the display control panel 42 can display the affirmative decision together with the distance that the biopsy needle 62 moves.

Conversely, if the biopsy needle movement distance calculator 110 receives information from the decision section 108, which indicates that calculation of the distance that the biopsy needle 62 moves is prohibited, then the biopsy needle movement distance calculator 110 does not calculate the distance that the biopsy needle 62 moves with respect to the biopsy region 36. In this case, the display unit 68 and/or the display control panel 42 displays only the negative decision.

Based on the distance calculated by the biopsy needle movement distance calculator 110, the biopsy needle drive controller 112 controls the biopsy hand assembly 38 to move the biopsy needle 62 to a given position.

The sampler 64 of the biopsy needle 62 is connected to a vacuum device (aspirating device) 116 through a vacuum hose (aspirating passage) 114. In a case where the vacuum device 116 starts an aspirating action while the biopsy needle 62 is inserted into the breast 22, the sampler 64 aspirates and extracts tissue from the biopsy region 36 in the vicinity of the sampler 64, under an aspirating action of the vacuum device 116.

Characteristic Functions of the Embodiment:

The mammographic system 12 incorporating the biopsy apparatus 10 according to the present embodiment is basically constructed as described above. Next, characteristic functions of the biopsy apparatus 10 according to the present embodiment will be described below.

According to characteristic functions of the biopsy apparatus 10, the biopsy needle 62 is inserted into a phantom 120 (see FIG. 5A), which simulates the breast 22, and extracts a portion of the phantom 120. After the portion of the phantom 120 has been extracted, radiation 24 is applied to the phantom 120 in order to acquire a radiographic image. Based on the acquired radiographic image of the phantom, a spatial range (second spatial range, aspiration range, sampling range) within which the sampler 64 of the biopsy needle 62 can actually sample tissue of the biopsy region 36 is measured before the biopsy procedure is carried out.

Characteristic functions of the biopsy apparatus 10 will be described in detail below with reference to FIGS. 5A through 14C. Components of the biopsy apparatus 10, which have not been specifically described with reference to FIGS. 1 through 4, will also be described below.

Figure 5A:
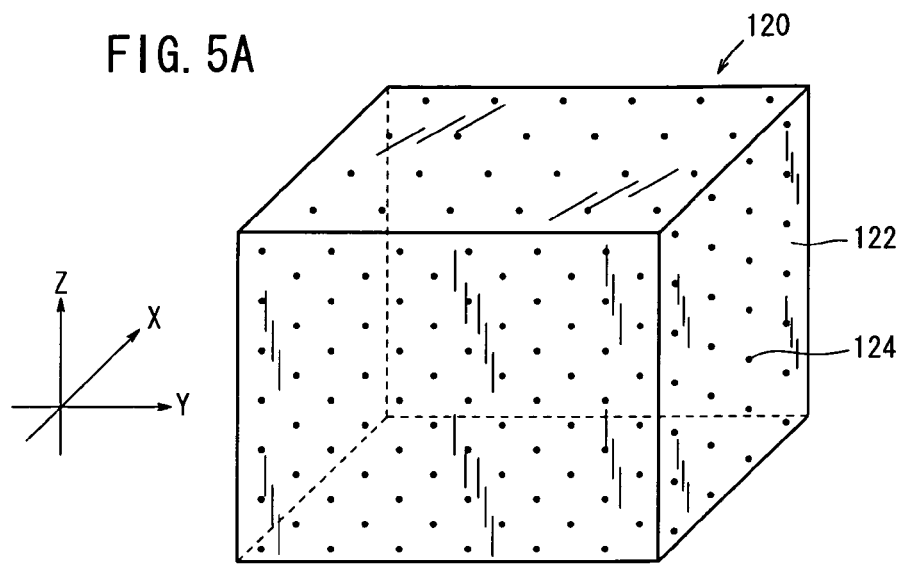
FIG. 5A is a perspective view of a phantom according to the embodiment of the present invention.
Figure 5B:
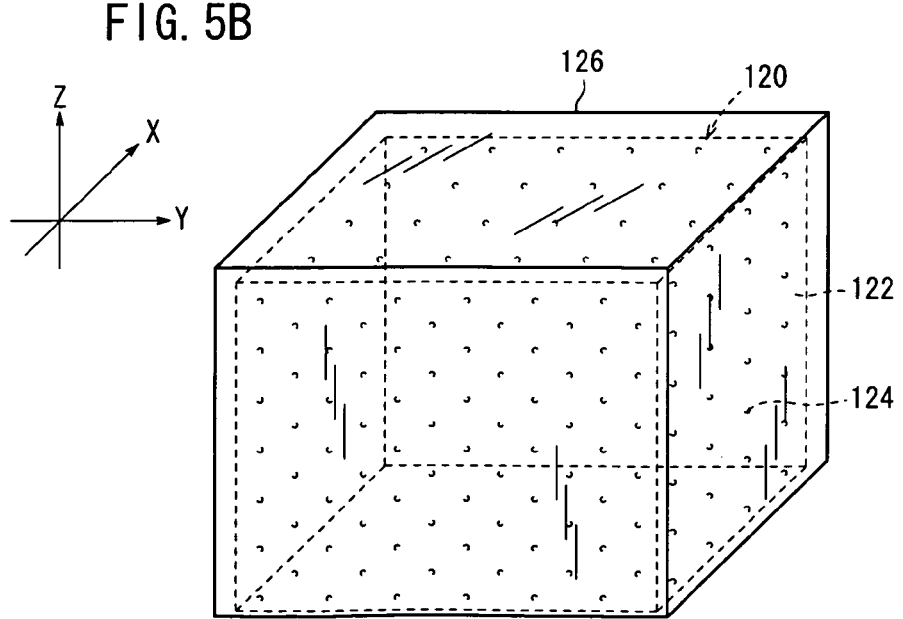
FIG. 5B is a perspective view of the phantom shown in FIG. 5A, which is housed in a receptacle.

As shown in FIG. 5A, the phantom 120 has a first member 122, which simulates the breast 22, and a plurality of second members 124 disposed in the first member 122, which simulate tissue (calcified tissue) of the biopsy region 36 in the breast 22. The phantom 120 is used as a device for training the doctor to insert the biopsy needle 62 into the first member 122, and to sample one of the second members 124 in the first member 122. The second members 124, each in the form of a particle, are disposed or distributed substantially uniformly throughout the first member 122, which is in the shape of a rectangular parallelepiped.

The first member 122 is made of a material that is permeable to radiation 24 and light and which can be aspirated by the sampler 64. The material may be gelatin or a polysaccharide. The polysaccharide may be a water-soluble natural polymer polysaccharide, which is produced by a microbial fermentation process, and which is of higher viscosity than gelatin, and more preferably, may be composed of gellan gum.

The second members 124 are made of a material that is less permeable to radiation 24 and light than the first member 122, or which is impermeable to radiation 24 and light. More specifically, the second members 124 are made from metal or ceramics, or more preferably, from lead or alumina (aluminum oxide). Each of the second members 124 is in the form of a particle having a diameter in a range from 100 µm to 500 µm, which is about the same size as actual calcified tissues in the breast 22. The size of each of the second members 124 is smaller than the outside diameter of the biopsy needle 62, and more preferably, is smaller than the inside diameter (about several mm) of a lumen 134 (see FIG. 6B) defined in the biopsy needle 62 and the opening 136 (see FIGS. 6A and 6B) defined as the sampler 64.

The phantom 120 is fabricated by dissolving a powder of gellan gum into water to thereby produce a sol, mixing a plurality of second members 124 in the form of particles with the sol, pouring the mixture into a molding frame (not shown) in the shape of a rectangular parallelepiped, solidifying the mixture into a gel, and removing the gel as the phantom 120. The phantom 120 thus fabricated is housed in a receptacle 126 (see FIG. 5B) that is permeable to radiation 24 and light. The first member 122, which is made of gel-like gellan gum, tends to get moldy if brought into contact with ambient air. If placed in the receptacle 126, the phantom 120 is isolated from ambient air surrounding the receptacle 126. The walls of the receptacle 126 are thin enough to be pierced by a pointed tip end 132 of the biopsy needle 62.

A process of inserting the biopsy needle 62 into the phantom 120 and extracting a portion of the phantom 120 with the sampler 64 of the biopsy needle 62, a process of capturing radiographic images of the phantom 120 after a portion thereof has been extracted by the biopsy needle 62, and a process of measuring a spatial range (second spatial range) within which the sampler 64 can extract or sample tissue of the biopsy region 36 based on the acquired radiographic images will be described in detail below with reference to FIGS. 6A through 13B.

The biopsy needle 62 includes a hollow tubular needle body 130 with a tip end 132 sharpened into a pointed shape. The needle body 130 has an opening 136 defined in a side wall near the tip end 132 thereof. The opening 136 is held in fluid communication with a lumen 134, which is defined in the needle body 130 and functions as the sampler 64. A hollow tubular cutter 138 is movably disposed in the lumen 134 for movement toward and away from the tip end 132. The lumen 134 and a lumen 140 defined in the tubular cutter 138 are connected to the vacuum device 116 through the vacuum hose 114 (see FIG. 4).

By operation of the vacuum device 116, the biopsy needle 62 operates to aspirate an object near the opening 136 into the lumen 134, under a vacuum that is present in the opening 136, the lumens 134, 140, and the vacuum hose 114, and cuts off the aspirated object by moving the tubular cutter 138 toward the tip end 132. This procedure is referred to as VAB (vacuum assisted biopsy).

In FIGS. 6A through 9B, the biopsy needle 62 is shown as exaggerated in order to illustrate structural details of the biopsy needle 62.

Figure 6A:
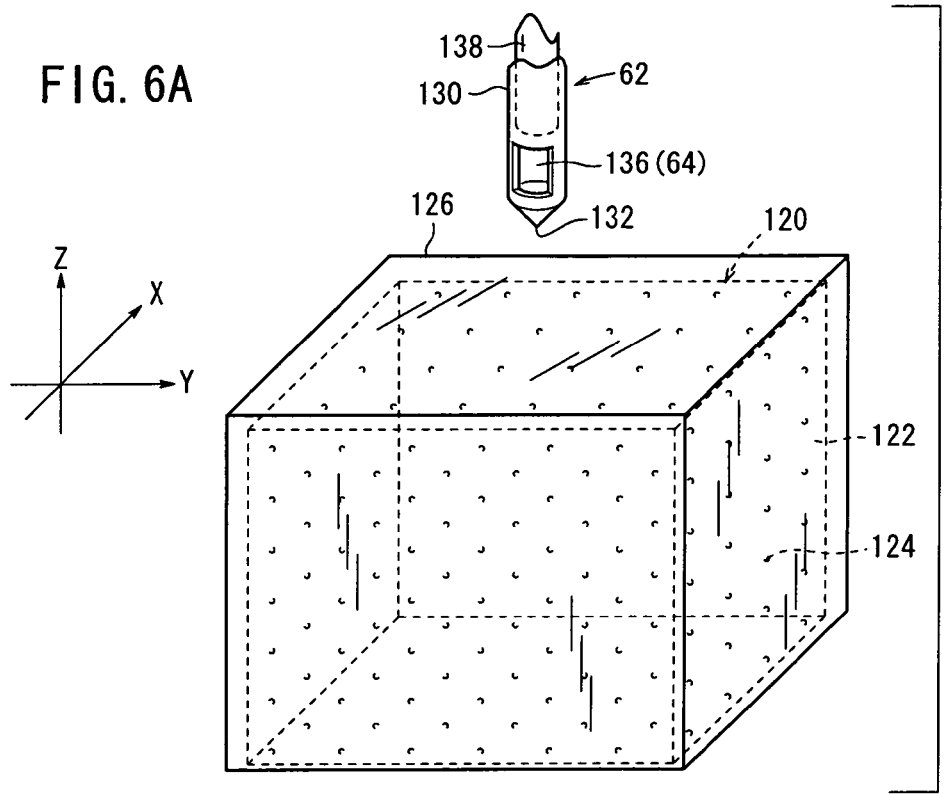
FIG. 6A is a perspective view of the phantom, which is housed in the receptacle, before a biopsy needle is inserted into the receptacle.
Figure 6B:
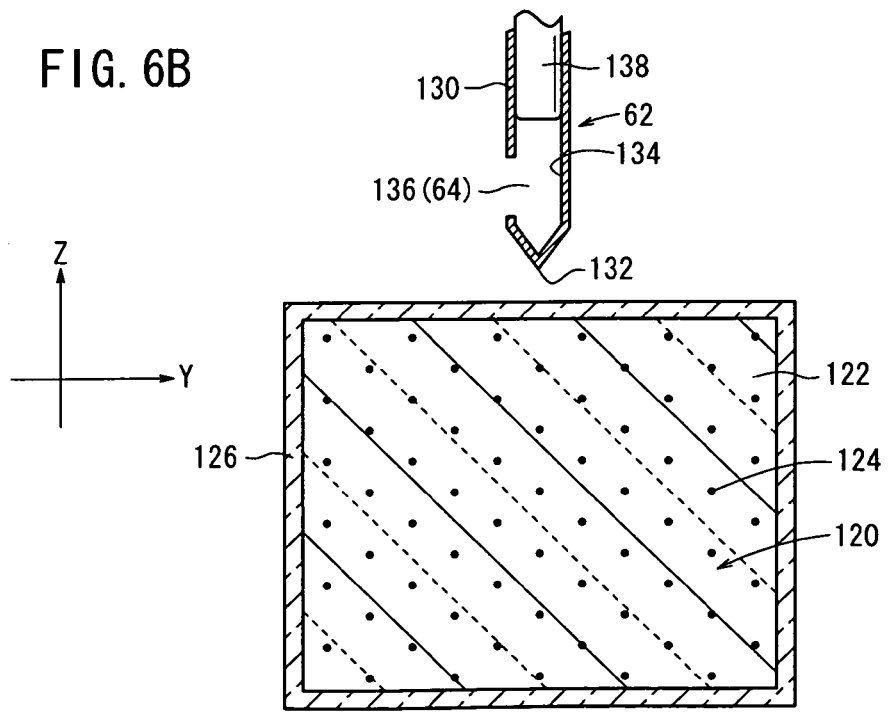
FIG. 6B is a cross-sectional view of the biopsy needle, the phantom, and the receptacle.
Figure 7A:
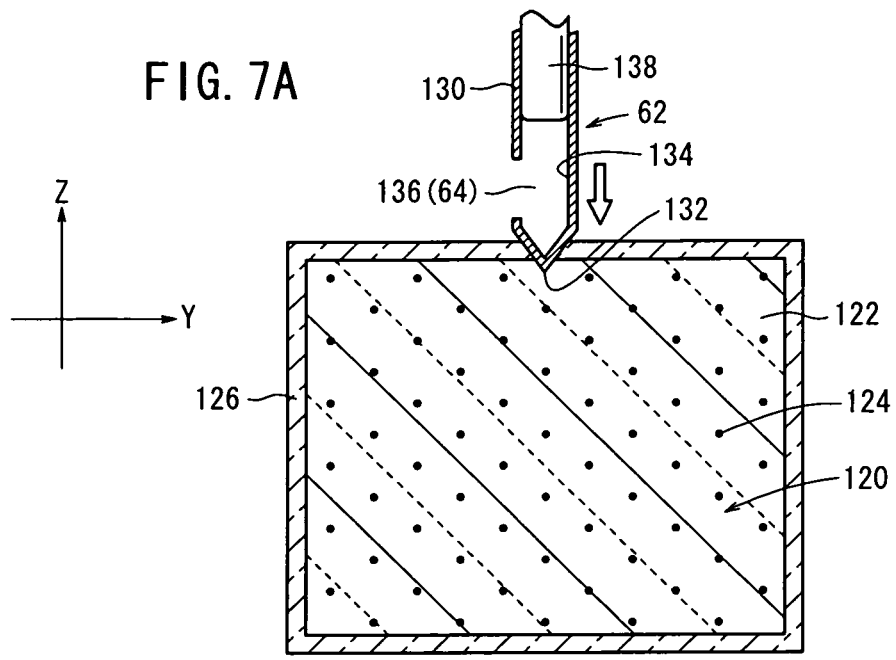
FIG. 7A is a cross-sectional view showing the manner in which a pointed tip end of the biopsy needle cuts into a portion of the receptacle.

The tip end 132 of the biopsy needle 62 is moved by the biopsy hand assembly 38 to a position above the phantom 120, as shown in FIGS. 6A and 6B. Then, the biopsy needle 62 is lowered toward the phantom 120. As shown in FIG. 7A, the tip end 132 of the biopsy needle 62 pierces the thin upper wall of the receptacle 126 and enters into the receptacle 126, whereupon the tip end 132 of the biopsy needle 62 reaches the upper surface of the phantom 120. At this time, the tip end 132 of the biopsy needle 62 may be pushed into the first member 122.

Figure 7B:
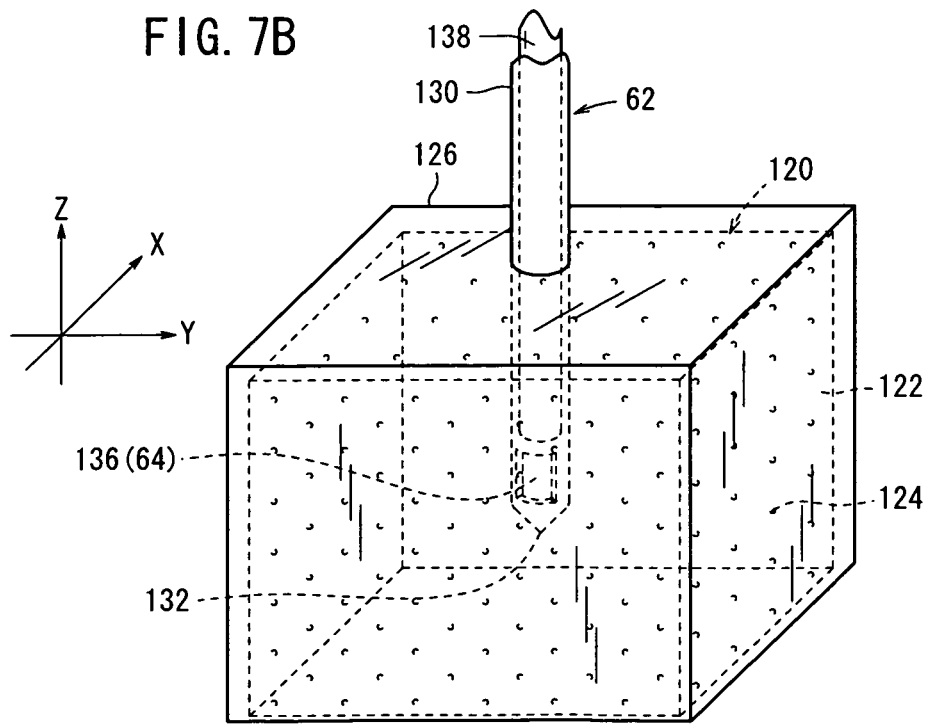
FIG. 7B is a perspective view showing the manner in which the biopsy needle is inserted into the phantom.
Figure 8A:
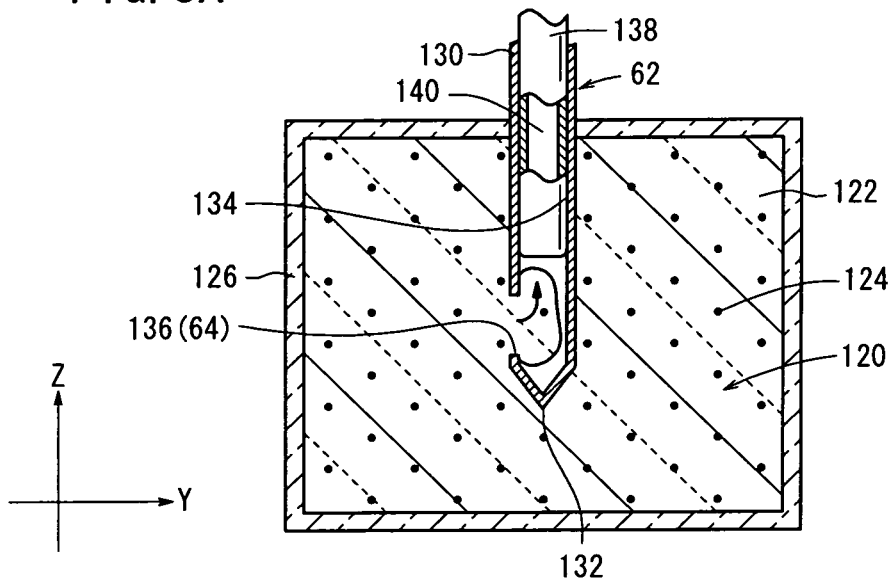
FIG. 8A is a cross-sectional view showing the manner in which the biopsy needle begins to aspirate a portion of the phantom.

Thereafter, as shown in FIGS. 7B and 8A, the biopsy needle 62 is further inserted until the tip end 132 thereof reaches a certain position inside the phantom 120.

The biopsy needle 62 may be moved manually by the doctor who operates the mammographic system 12, or may be moved automatically by the biopsy hand assembly 38. In the case that the biopsy needle 62 is moved from the position shown in FIG. 7A to the position shown in FIGS. 7B and 8A, the doctor may operate an operating console (not shown) of the biopsy needle 62, for example, so as to force the biopsy needle 62, in one stroke under the bias of a spring, to the position located in the phantom 120. In a subsequent radiographic image capturing process performed on the phantom 120, radiographic images may be acquired of a cavity (first spatial range, aspiration range, sampling range) that is formed by extracting a portion of the phantom 120. It is inconsequential whether or not one of the second members 124 actually is extracted. The depth at which the biopsy needle 62 is inserted into the phantom 120, and the position at which the biopsy needle 62 is inserted into the phantom 120, may be selected appropriately.

As shown in FIG. 8A, the vacuum device 116 (see FIG. 4), which is connected to the lumen 134 of the biopsy needle 62 and the lumen 140 of the tubular cutter 138, is actuated in order to aspirate through the opening 136 and into the lumen 134 a portion of the phantom 120 that faces toward the opening 136, e.g., one of the second members 124 and a portion of the first member 122 in the vicinity of the second member 124.

Figure 8B:
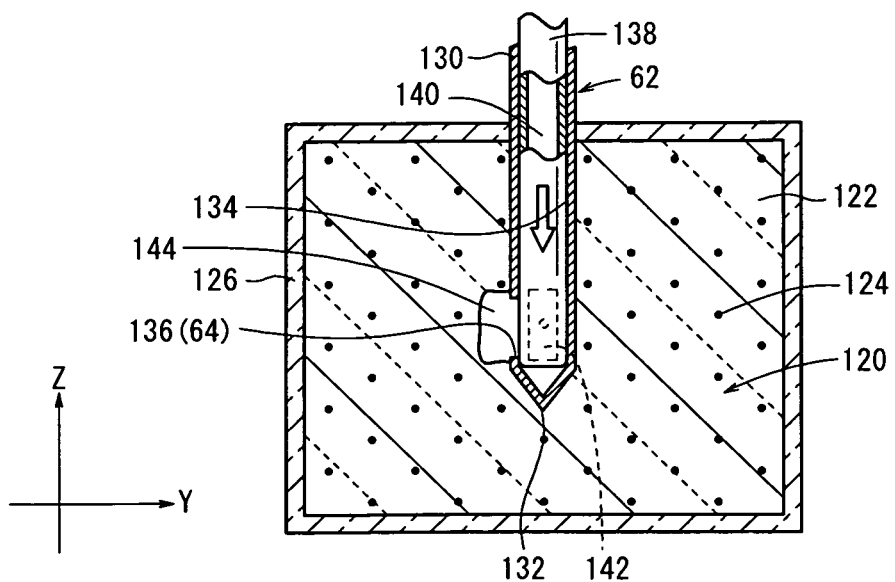
FIG. 8B is a cross-sectional view showing the manner in which the biopsy needle has extracted a portion of the phantom as a sample.

While the portion of the lumen 134 that faces the opening 136 is being filled with the portion of the phantom 120 under suction from the vacuum device 116, the tubular cutter 138 is lowered toward the tip end 132, thereby cutting off the portion of the phantom 120 and extracting the severed portion as a cylindrical sample 142 (see FIG. 8B). Therefore, a cavity 144, from which the portion of the phantom 120 has been cut off by the tubular cutter 138, is formed in the phantom 120 in the vicinity of the opening 136. Movement of the tubular cutter 138 may be controlled by the biopsy needle drive controller 112.

Figure 9A:
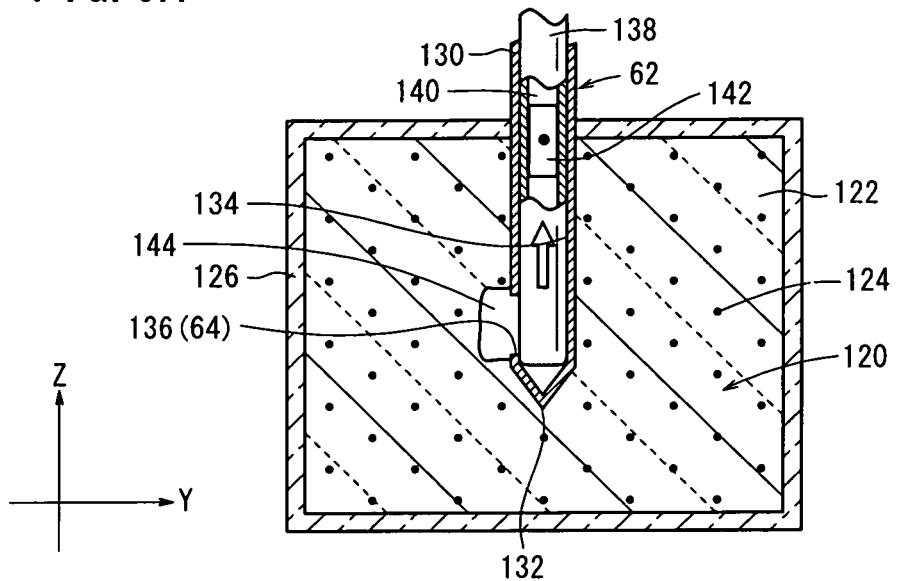
FIG. 9A is a cross-sectional view showing the manner in which the sample is drawn through the biopsy needle.
Figure 9B:
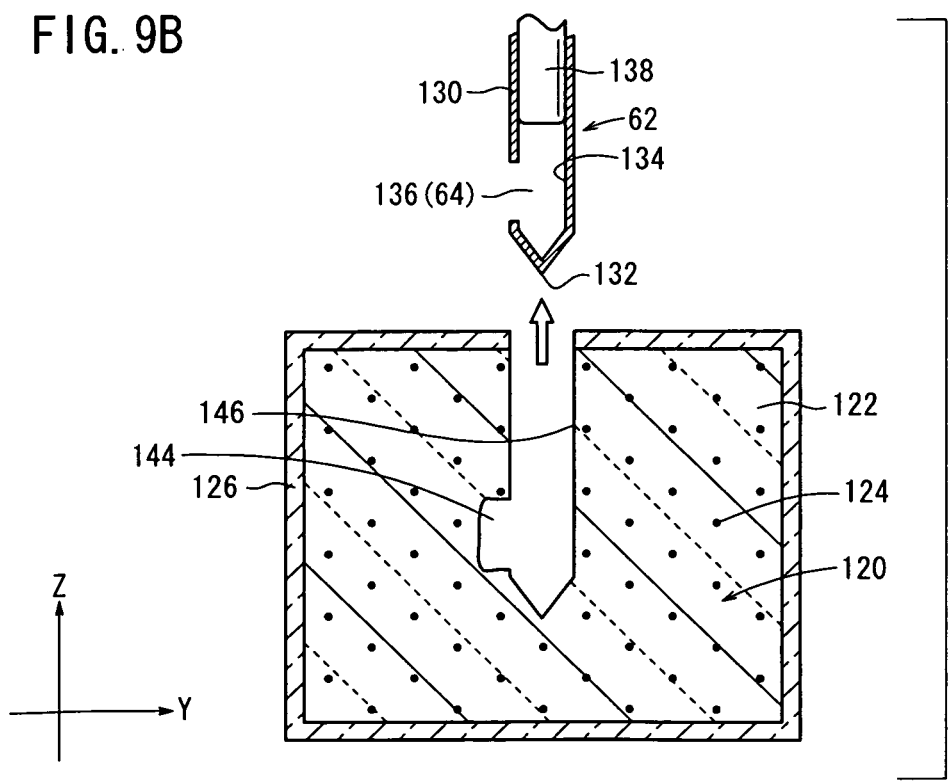
FIG. 9B is a cross-sectional view showing the manner in which the biopsy needle is pulled out from the phantom and the receptacle.

Then, as shown in FIG. 9A, the vacuum device 116 is actuated to draw the sample 142 upwardly through the lumens 134 and 140. At the same time, as shown in FIG. 9B, the biopsy needle 62 is pulled upwardly out of the phantom 120 and moved upwardly away from the phantom 120 and the receptacle 126, thereby leaving a passage 146 connected to the cavity 144 in the phantom 120 and through which the biopsy needle 62 has been pulled out. The sample 142 is discharged out of the vacuum hose 114 or the vacuum device 116.

Figure 10A:
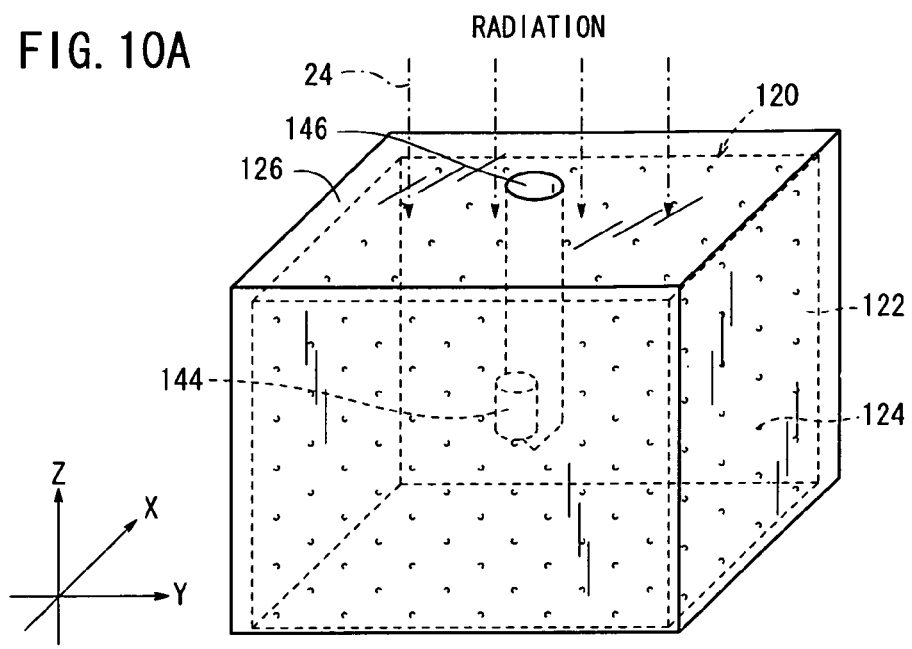
FIG. 10A is a perspective view showing the manner in which radiation is applied to the phantom and the receptacle from which the biopsy needle has been pulled out, along a direction in which the biopsy needle has been inserted into the phantom.
Figure 10B:
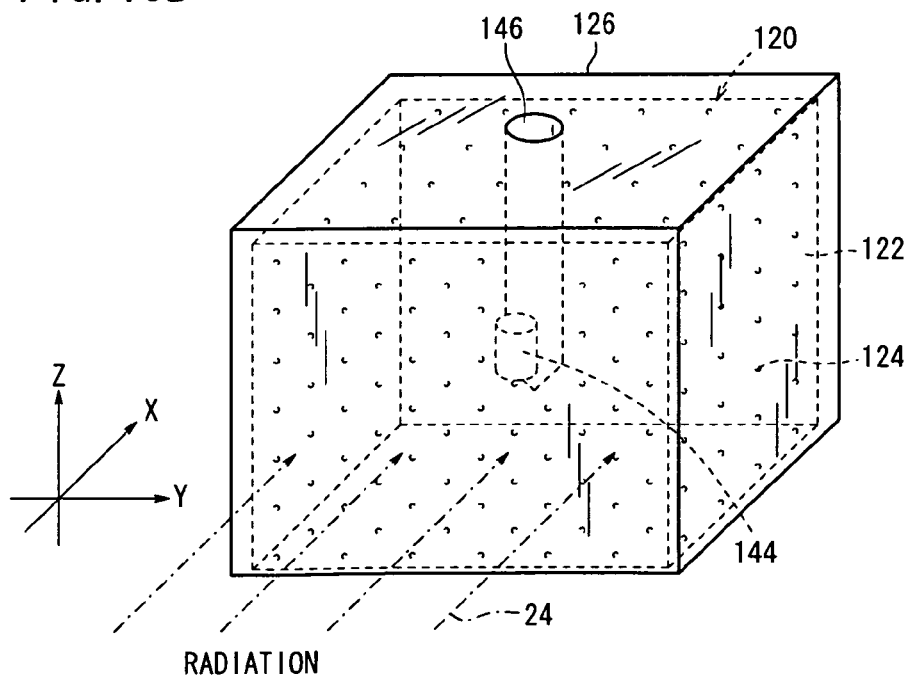
FIG. 10B is a perspective view showing the manner in which radiation is applied to the phantom and the receptacle from which the biopsy needle has been pulled out, along a direction substantially perpendicular to the direction in which the biopsy needle has been inserted into the phantom.

Then, as shown in FIG. 10A, a first radiographic capturing process is performed to apply radiation 24 to the phantom 120 along the direction in which the passage 146 is formed, i.e., along the direction in which the biopsy needle 62 was inserted into the phantom 120, or along the direction indicated by the arrow Z. At this time, a radiographic image of the phantom 120, i.e., a first image of the phantom 120, is generated along an X-Y plane perpendicular to the directions indicated by the arrow Z. Thereafter, as shown in FIG. 10B, a second radiographic capturing process is performed to apply radiation 24 to the phantom 120 along a direction perpendicular to the direction in which the passage 146 is formed. A radiographic image of the phantom 120, i.e., a second image of the phantom 120, is generated along a Y-Z plane perpendicular to the directions indicated by the arrow X.

FIGS. 11A and 11B are schematic views illustrative of the radiographic image capturing processes performed as shown in FIGS. 10A and 10B, which are performed by the mammographic system 12. In FIGS. 11A and 11B, for illustrative purposes, the receptacle 126 and other parts are omitted from illustration.

FIG. 11A shows the first radiographic image capturing process. As shown in FIG. 11A, the phantom 120, which is held between the compression plate 34 and the image capturing base 32, is irradiated with radiation 24c from the radiation source 26 that is disposed in the position C. The compression plate 34 and the image capturing base 32 hold the phantom 120 along the directions indicated by the arrow Z, in a manner so as to prevent the phantom 120 from moving. The cavity 144 and the passage 146 in the phantom 120 are positioned directly below the opening 54 in the compression plate 34. In other words, FIG. 11A illustrates application of radiation 24c to the phantom 120, while the phantom 120 is being held between the compression plate 34 and the image capturing base 32, and after a portion of the phantom 120 held between the compression plate 34 and the image capturing base 32 has been extracted by the biopsy needle 62, in the same manner as with a biopsy procedure performed on the breast 22.

In FIGS. 10A and 11A, since radiation 24 (24c) is applied to the phantom 120 along the direction in which the cavity 144 and the passage 146 are formed, i.e., along the direction in which the biopsy needle 62 was inserted into the phantom 120, the solid-state detector 30 converts the radiation 24 (24c) that has passed through the phantom 120 into a radiographic image on a projection plane (X-Y plane), which is substantially perpendicular to the direction in which the biopsy needle 62 was inserted into the phantom 120. The detector controller 88 (see FIG. 4) stores the radiographic image on the projection plane in the image information storage section 90.

FIG. 11B shows the second radiographic image capturing process. As shown in FIG. 11B, in the second radiographic image capturing process, the phantom 120 having a portion extracted therefrom is placed again on the image capturing base 32, such that the cavity 144 and the passage 146 extend along the directions indicated by the arrow X. Thereafter, the phantom 120 is held again between the compression plate 34 and the image capturing base 32, and is irradiated with radiation 24c from the radiation source 26, which is disposed in the position C.

In FIG. 11B, since radiation 24 (24c) is applied to the phantom 120 along a direction substantially perpendicular to the direction in which the cavity 144 and the passage 146 are formed, i.e., along the direction in which the biopsy needle 62 was inserted into the phantom 120, the solid-state detector 30 converts the radiation 24 (24c) that has passed through the phantom 120 into a radiographic image on a projection plane (X-Y plane), which is parallel to the direction in which the biopsy needle 62 was inserted in the phantom 120. The detector controller 88 (see FIG. 4) stores the radiographic image on the projection plane in the image information storage section 90.

In FIG. 11B, as the phantom 120 is turned over on the image capturing base 32 from the position shown in FIG. 11A and is held again between the compression plate 34 and the image capturing base 32, radiation 24c is applied to the phantom 120 along the direction indicated by the arrow Z. Therefore, the direction in which radiation 24c is applied to the phantom 120 in FIG. 11B differs from the direction in which radiation 24c is applied to the phantom 120 in FIG. 10B, i.e., along the direction indicated by the arrow X.

Figure 12A:
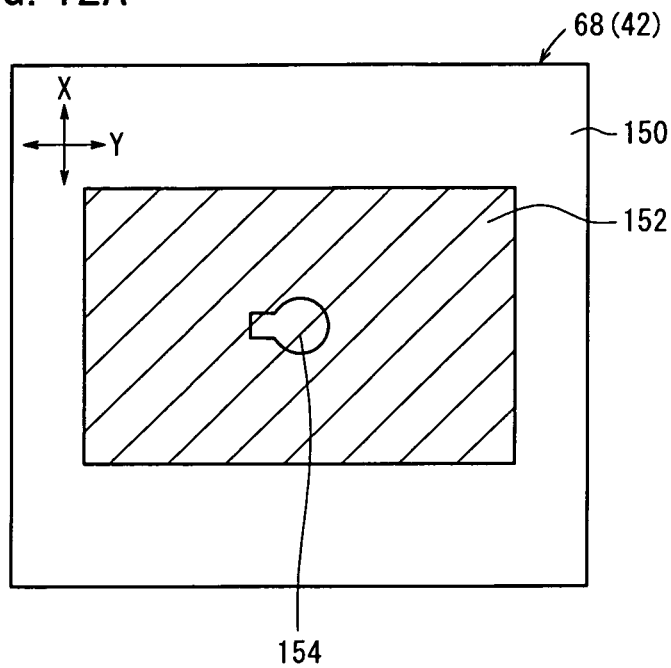
FIGS. 12A and 12B are views showing radiographic images obtained respectively from the radiographic image capturing processes illustrated in FIGS. 11A and 11B.
Figure 12B:
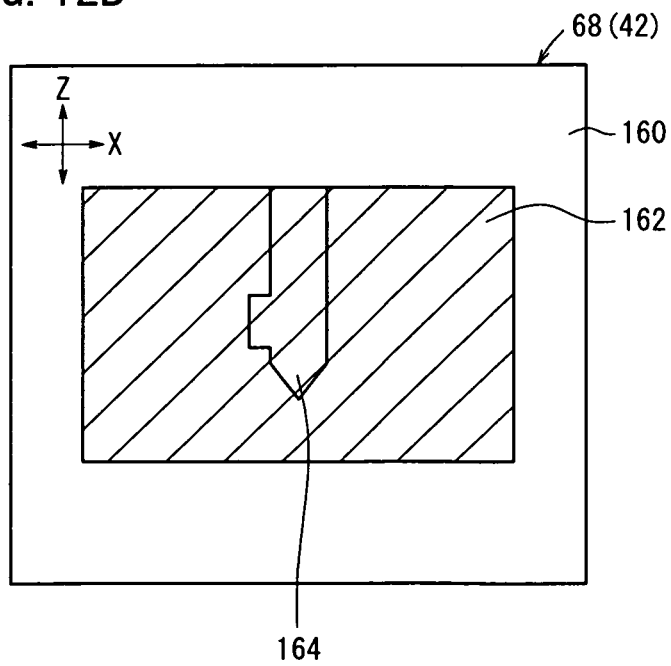

FIG. 12A shows the radiographic image captured in the first radiographic image capturing process shown in FIG. 11A, which is displayed on the display unit 68 and/or the display control panel 42. FIG. 12B shows the radiographic image captured in the second radiographic image capturing process shown in FIG. 11B, which is displayed on the display unit 68 and/or the display control panel 42. The radiographic images shown in FIGS. 12A and 12B represent images of the phantom 120, which have not yet been processed by the CAD processor 92 (see FIG. 4).

In FIGS. 12A and 12B, the screen of the display unit 68 and/or the display control panel 42 display respective images 152, 162 of the phantom 120 along with respective blank images 150, 160 outside of the images 152, 162. The images 152, 162 include images 154, 156 therein, respectively, each of which is representative of the cavity 144 and the passage 146. With the displayed images shown in FIGS. 12A and 12B, however, it is difficult to identify the range (second spatial range) of the cavity 144 from the images 154, 164, because of the low contrast ratio between the images 152, 162 and the images 154, 164.

Figure 13A:
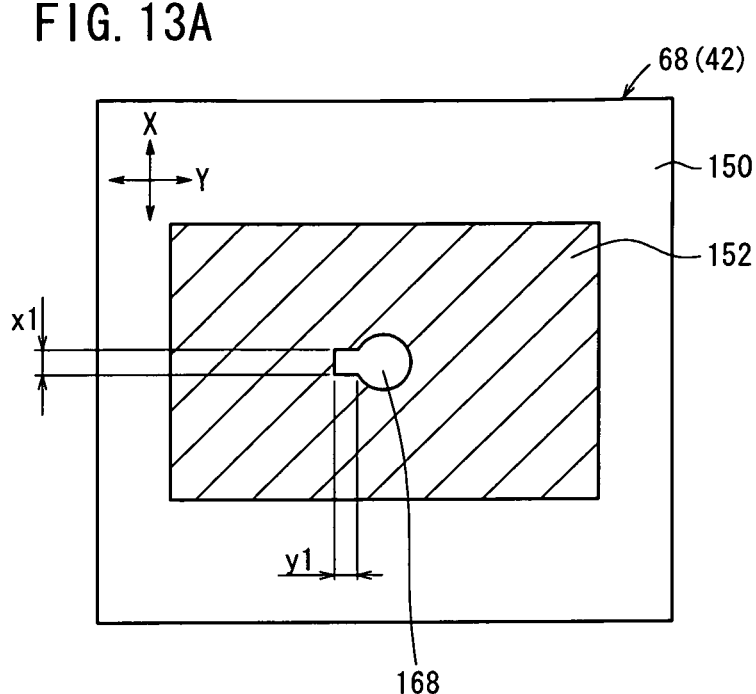
FIGS. 13A and 13B are views showing radiographic images produced in a case where the radiographic images shown in FIGS. 12A and 12B are processed by an image processing sequence.
Figure 13B:
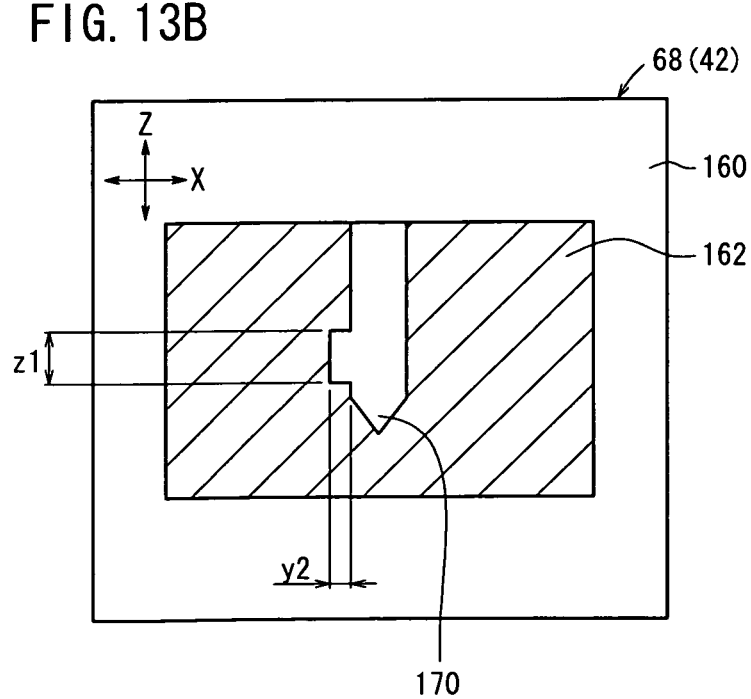

The CAD processor 92 performs certain image processing sequences, such as contrast enhancement and edge enhancement, on the radiographic images, thereby generating the radiographic images shown in FIGS. 13A and 13B, which exhibit a high contrast ratio between the images 152, 162 and the images 168, 170 that are representative of the cavity 144 and the passage 146. FIG. 13A shows a processed radiographic image, which is generated by performing image processing sequences on the radiographic image shown in FIG. 12A. FIG. 13B shows a processed radiographic image, which is generated by performing image processing sequences on the radiographic image shown in FIG. 12B. The CAD processor 92 outputs the radiographic images to the aspiration space calculator 94 (see FIG. 4).

The aspiration space calculator 94 measures lengths (widths) x1, y1, y2, z1 of the cavity 144 in the directions indicated by the arrows X, Y, Z (see FIGS. 8B through 11B) in the images 168, 170 contained within the radiographic images shown in FIGS. 13A and 13B. Then, depending on the measured lengths, the aspiration space calculator 94 inversely calculates the lengths (ranges) in the directions indicated by the arrows X, Y, Z of the actual cavity 144. Finally, the aspiration space calculator 94 defines the inversely calculated lengths as a first spatial range aspirated by the sampler 64, and stores the first spatial range and the measured radiographic images in the phantom aspiration range storage section 96.

Ideally, the lengths y1, y2 should preferably be equal to each other (y1=y2). However, as shown in FIGS. 11A and 11B, since the distance from the radiation source 26 to the cavity 144 in the first radiographic image capturing process and the distance from the radiation source 26 to the cavity 144 in the second radiographic image capturing process differ from each other, the lengths y1, y2 may also differ from each other (y1≠y2). In order to accurately determine the range in the directions indicated by the arrow Y, the aspiration space calculator 94 may determine an average y of the lengths y1, y2 according to the equation y=(y1+y2)/2, and then from the average y, determine the range of the actual cavity 144 in the directions indicated by the arrow Y.

In addition to the first spatial range, the phantom aspiration range storage section 96 may store therein the three-dimensional coordinate position of the biopsy needle 62 that is inserted into the phantom 120.

As described above, the aspiration space calculator 94 measures lengths (widths) x1, y1, y2, z1 of the cavity 144 in the directions indicated by the arrows X, Y, Z. Alternatively, the aspiration space calculator 94 may check whether or not the biopsy needle 62 has extracted a portion of the phantom 120 at each location in the radiographic image, and may store in the phantom aspiration range storage section 96 three-dimensional coordinate data (x, y, z) of each location together with the result of the check, as data indicative of the first spatial range.

If such data are stored in the phantom aspiration range storage section 96, then data representative of a second spatial range, to be described later, which are stored in the aspiratable range storage section 98, should preferably be data representative of three-dimensional coordinate data (x, y, z) of each location in the breast 22, and the result of the check as to whether or not the biopsy needle 62 has extracted a portion of the breast 22 at each location.

In the following description, it is assumed that a first spatial range based on the lengths x1, y1, y2, z1 is used.

Since the phantom 120 and the breast 22 have different properties, the spatial range (first spatial range) within which the phantom 120 can be sampled by the biopsy needle 62 and the spatial range (second spatial range) within which the breast 22 can be sampled by the biopsy needle 62 may differ from each other.

The corrective data storage section 100 (see FIG. 4) stores corrective data based on properties of the phantom 120 and properties of the breast 22.

The corrective data refer to data based on the spatial range within which the biopsy needle 62 can extract a portion of the phantom 120, and the spatial range within which the biopsy needle 62 can extract tissue of the biopsy region 36, or data based on property values of the substance (the first member 122) that makes up the phantom 120 and property values of the substance that makes up the breast 22.

The data based on the spatial ranges refer to image data representing extraction of ranges (spatial ranges) of the biopsy needle 62 that are formed in the phantom 120 and the breast 22 after a portion of the phantom 120 and tissue of the breast 22 have been extracted by the biopsy needle 62, which was inserted into the phantom 120 and the breast 22. The data based on property values refer to a modulus of elasticity of the first member 122 of the phantom 120 and a modulus of elasticity of the substance of the breast 22.

The aspiration space calculator 94 reads radiographic images from the phantom aspiration range storage section 96, and also reads image data representing the extraction ranges of the biopsy needle 62 from the corrective data storage section 100. Thereafter, the aspiration space calculator 94 identifies the location of the cavity 144 (image area of the first spatial range) within the read radiographic images from the difference in contrast between the images 152, 162 and the cavities 144 in the images 168, 170. The aspiration space calculator 94 determines the second spatial range of the breast 22 based on a comparison between the identified location of the cavity 144 and the image data representing the extraction ranges.

Alternatively, the aspiration space calculator 94 may read from the phantom aspiration range storage section 96 a range in the directions indicated by the arrows X, Y, Z of the cavity 144 representative of the first spatial range, and may also read the moduli of elasticity from the corrective data storage section 100. In this case, the aspiration space calculator 94 can determine a range in the directions indicated by the arrows X, Y, Z representing the second spatial range in the breast 22, by multiplying the range in the directions indicated by the arrows X, Y, Z of the cavity 144 by a corrective coefficient based on the moduli of elasticity.

The aspiration space calculator 94 then stores in the aspiratable range storage section 98 the determined second spatial range of the breast 22 or the determined range in the directions indicated by the arrows X, Y, Z representing the second spatial range, as data representative of a range within which the biopsy needle 62 can actually aspirate tissue from the breast 22.

The aspiration space calculator 94 may determine the second spatial range according to either one of a process for determining a second spatial range based on image data representing extraction ranges and a process for determining a second spatial range based on a corrective coefficient, or alternatively according to both of these two processes, for obtaining higher accuracy upon calculation of the second spatial range.

The second spatial range within which the sampler 64 of the biopsy needle 62 can extract tissue from the biopsy region 36 depends on characteristics of the biopsy needle 62, characteristics of the vacuum hose 114, and characteristics of the vacuum device 116.

The changing factor data storage section 102 stores changing factor data representing changing factors of the second spatial range.

The changing factor data represent characteristics of the biopsy needle 62, characteristics of the vacuum hose 114, and characteristics of the vacuum device 116, which serve as changing factors of the second spatial range. More specifically, the changing factor data refer to the following data:

Characteristics of the biopsy needle 62 include the type of the biopsy needle 62, the shape of the tip end 132, the area of the opening 136, the diameter of the needle body 130, the shape of the opening 136, and the serial number of the biopsy needle 62.

Characteristics of the vacuum hose 114 include the type of vacuum hose 114, the inside diameter of the vacuum hose 114, the total time that the vacuum hose 114 has been used, the number of examinees 20 on which biopsies have been performed using the vacuum hose 114 or the number of times that biopsies have been performed using the vacuum hose 114, the time over which the vacuum hose 114 has been used after maintenance thereof, the number of examinees 20 on which the vacuum hose 114 has been used or the number of times that aspirations have been carried out using the vacuum hose 114.

Characteristics of the vacuum device 116 include the type of vacuum device 116, vacuum pressures (a pressure setting value, a maximum value or a minimum value of a vacuum pressure that changes with respect to the pressure setting value, and a measured vacuum pressure detected in real time), the total time that the vacuum device 116 has been used, the number of examinees 20 on which biopsies have been performed using the vacuum device 116 or the number of times that biopsies have been performed using the vacuum device 116, the time over which the vacuum device 116 has been used after maintenance thereof, the number of examinees 20 on which the vacuum device 116 has been used or the number of times that aspirations have been carried out using the vacuum device 116.

In a case where the indicating unit 70 indicates a biopsy region 36 on which a biopsy is to be performed, the aspiration space calculator 94 reads the changing factor data from the changing factor data storage section 102, and also reads the second spatial range (as represented by the range in the directions indicated by the arrows X, Y, Z) from the aspiratable range storage section 98.

Then, the aspiration space calculator 94 corrects the second spatial range based on the changing factor data, and outputs the corrected second spatial range and the changing factor data to the decision section 108. Alternatively, the aspiration space calculator 94 may not correct the second spatial range, but instead may output the read second spatial range and the changing factor data corresponding thereto to the decision section 108.

If the aspiration space calculator 94 corrects the second spatial range based on the changing factor data, then the aspiration space calculator 94 may store the corrected second spatial range (second spatial range depending on the changing factor data) in the aspiratable range storage section 98. In this case, a second spatial range for each type of biopsy needle 62 may be stored in the aspiratable range storage section 98, so that each time a biopsy procedure is performed, the aspiration space calculator 94 may read a second spatial range into the decision section 108.

The decision section 108 determines whether or not the biopsy needle 62 can extract tissue of the biopsy region 36 based on the second spatial range (which is corrected based on the changing factor data), the target coordinate position, the three-dimensional coordinate position of the biopsy needle 62, the position of the lower surface of the compression plate 34 along the directions indicated by the arrow Z, and positional data of the opening 54.

More specifically, the decision section 108 compares the second spatial range determined by the aspiration space calculator 94 with a threshold value based on the changing factor data (a minimum value of the second spatial range within which the sampler 64 can extract tissue of the biopsy region 36 at the time that the sampler 64 and the biopsy region 36 face toward each other). If the determined second spatial range is greater than the threshold value, then the decision section 108 judges that the biopsy needle 62 can extract tissue of the biopsy region 36. If the determined second spatial range is smaller than the threshold value, then the decision section 108 judges that the biopsy needle 62 cannot extract tissue from the biopsy region 36.

Figure 14A:
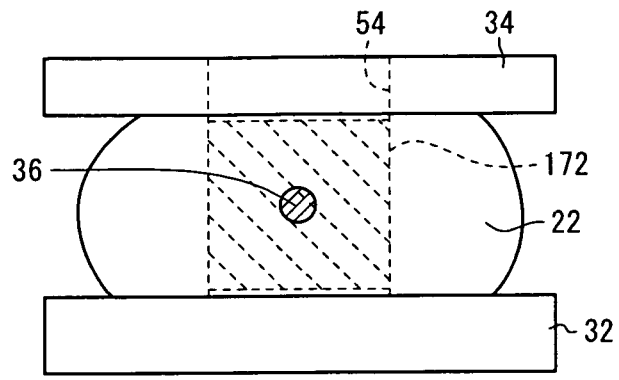
FIGS. 14A through 14C are views showing the relationship between a position of a biopsy region and a range within which the biopsy region can be sampled.
Figure 14B:
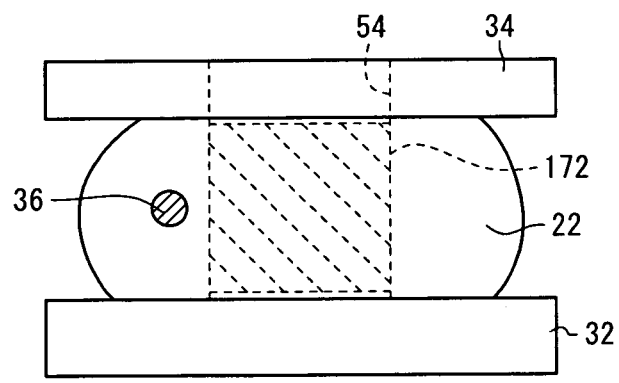
Figure 14C:
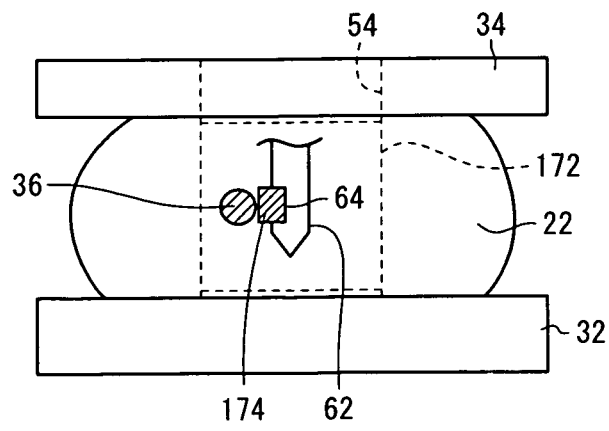

As shown in FIGS. 14A through 14C, the compression plate 34 has the opening 54 defined therein. The biopsy needle 62 is movable along the directions indicated by the arrow Z. A region of the compressed breast 22, which is positioned between the opening 54 of the compression plate 34 and the image capturing base 32, serves as an extractable range (insertable range) 172 within which the sampler 64 of the biopsy needle 62 can extract tissue of the biopsy region 36.

In addition to the above decision process, the decision section 108 also is capable of determining whether or not the biopsy region 36 falls within the extractable range 172.

If the biopsy region 36 falls within the extractable range 172, as shown in FIG. 14A, then the decision section 108 judges that the biopsy needle 62 is capable of extracting tissue of the biopsy region 36. If the position of the biopsy region 36 falls outside of the extractable range 172, as shown in FIG. 14B, or if the biopsy needle 62 is unable to aspirate tissue from the biopsy region 36 because the aspiration range 174 (second spatial range) of the sampler 64 is too small, even though the biopsy region 36 lies within the extractable range 172, then the decision section 108 judges that the biopsy needle 62 cannot extract tissue of the biopsy region 36.

The decision section 108 may identify the extractable range 172 using the position of the lower surface of the compression plate 34 along the directions indicated by the arrow Z, the positional data of the opening 54, and the positional data of the image capturing base 32. Also, the decision section 108 may determine whether or not the biopsy region 36 falls within the extractable range 172 based on the identified extractable range 172, the position of the biopsy region 36, and the aspiration range 174.

Results of the above decision processes performed by the decision section 108 are displayed on the display unit 68 and/or the display control panel 42. If the results are affirmative, i.e., if the results indicate permission to perform a biopsy, then the biopsy needle movement distance calculator 110 is allowed to calculate the distance that the biopsy needle 62 moves. If the results are negative, i.e., if the results indicate prohibition of biopsy, then the biopsy needle movement distance calculator 110 is prohibited from calculating the distance that the biopsy needle 62 moves.

In the above description, a first spatial range is measured based on the two-dimensional images 152, 154, 162, 164, 168, 170, a second spatial range is determined using the measured first spatial range, and the determined second spatial range is corrected. As described above, since the CAD processor 92 is capable of generating three-dimensional radiographic images, a three-dimensional radiographic image of the phantom 120 may be generated, a first spatial range may be measured based on the generated three-dimensional radiographic image, a second spatial range may be determined using the measured first spatial range, and the determined second spatial range may be corrected.

Operations of the Embodiment:

Characteristic functions of the biopsy apparatus 10 according to the present embodiment have been described above.

A method of measuring a spatial range (spatial range measuring method) using the biopsy apparatus 10 and the phantom 120, and a biopsy procedure using the biopsy apparatus 10 and the mammographic system 12 will be described below with reference to the flowcharts shown in FIGS. 15 and 16. FIGS. 1 through 14C will also be referred to as necessary in describing the spatial range measuring method and the biopsy procedure with reference to the flowcharts shown in FIGS. 15 and 16.

First, the spatial range measuring method using the biopsy apparatus 10 and the phantom 120 will be described below with reference to FIG. 15.

In step S1 shown in FIG. 15, a doctor who handles the biopsy apparatus 10 establishes image capturing conditions depending on the phantom 120 (see FIGS. 5A and 5B) using the image capturing condition setting section 80 (see FIG. 4). The established image capturing conditions are set in the radiation source drive controller 82.

In step S2, the doctor positions the phantom 120. More specifically, the doctor places the receptacle 126 housing the phantom 120 therein in a given position, which faces toward the opening 54, on the image capturing base 32, and then operates the compression plate drive controller 84 to move the compression plate 34 toward the image capturing base 32 in the direction indicated by the arrow Z. The compression plate 34 positions the receptacle 126 in a manner to keep the receptacle 126 immovable on the image capturing base 32. The receptacle 126 is held in position by the image capturing base 32 and the compression plate 34. The compression plate position calculator 86 calculates the position of the lower surface of the compression plate 34 with respect to the origin O (see FIG. 3) in the directions indicated by the arrow Z, based on initial positional data of the compression plate 34 and the output signal from the displacement distance detector 50.

In step S3, if the calculated position of the lower surface of the compression plate 34 in the directions indicated by the arrow Z is a position that serves to hold the receptacle 126, then the biopsy needle drive controller 112 moves the biopsy needle 62 until the biopsy needle 62 becomes inserted into the phantom 120. More specifically, the biopsy needle drive controller 112 moves the first arm 58 and the second arm 60 in the X-Y plane in order to position the biopsy needle 62 in a position above the opening 54, which faces toward a given insertion position, and then moves the biopsy needle 62 toward the image capturing base 32. The tip end 132 of the biopsy needle 62 breaks through the receptacle 126 into the first member 122 (see FIG. 7A), until the tip end 132 arrives at a certain position in the phantom 120 (see FIG. 7B). As described above, the biopsy needle 62 may be moved in the directions indicated by the arrow Z either automatically by the biopsy hand assembly 38 or manually by the doctor.

In step S4, the vacuum device 116 (see FIG. 4) starts an aspirating action. The sampler 64 aspirates and extracts tissue of the biopsy region 36 in the vicinity of the sampler 64 under the aspirating action of the vacuum device 116. More specifically, by operation of the vacuum device 116, the biopsy needle 62 aspirates into the lumen 134 a portion of the phantom 120 located near the opening 136 (see FIG. 8A). The tubular cutter 138 then is moved toward the tip end 132 of the biopsy needle 62, thereby cutting off the aspirated portion of the phantom 120 and extracting the severed portion as a cylindrical sample 142 (see FIG. 8B). As a consequence, a cavity 144, from which a portion of the phantom 120 has been cut off by the tubular cutter 138, is formed in the phantom 120 in the vicinity of the opening 136.

The sample 142 is drawn upwardly through the lumens 134, 140 under the vacuum developed by the vacuum device 116 (see FIG. 9A). The sample 142 is discharged out of the vacuum hose 114 or the vacuum device 116. Thereafter, in step S5, the biopsy needle 62 is pulled upwardly out of the phantom 120 and is moved upwardly away from the phantom 120 and the receptacle 126, so as to leave a passage 146 in the phantom 120 through which the biopsy needle 62 has been pulled out.

In step S6, providing that the biopsy needle 62 has been moved away from the phantom 120 and the receptacle 126, and the vacuum device 116 has been shut down, the radiation source drive controller 82 energizes the radiation source 26 to perform a first radiographic image capturing process on the phantom 120. In the first radiographic image capturing process, the radiation source 26 applies radiation 24c to the phantom 120 from the position C (see FIG. 11A). The radiation 24c passes through the phantom 120 and is detected by the solid-state detector 30 in the image capturing base 32, as radiation representing a radiographic image of the phantom 120. In step S7, the detector controller 88 controls the solid-state detector 30 to acquire a radiographic image from the detected radiation, and to store the acquired radiographic image in the image information storage section 90.

After completion of the first radiographic image capturing process, the compression plate drive controller 84 moves the compression plate 34 upwardly to release the phantom 120 from the compression plate 34 and the image capturing base 32. Since the compression plate position calculator 86 has calculated the position of the lower surface of the compression plate 34 with respect to the origin O in the directions indicated by the arrow Z, the console 40 can easily recognize that the phantom 120 has been released, based on the calculated position of the lower surface of the compression plate 34.

Then, the doctor turns over the phantom 120 from the position shown in FIG. 11A into the position shown in FIG. 11B. Thereafter, the compression plate drive controller 84 moves the compression plate 34 toward the image capturing base 32, in order to hold the phantom 120 in position between the compression plate 34 and the image capturing base 32. The console 40 can easily recognize that the phantom 120 is held again, based on the position of the lower surface of the compression plate 34 in the directions indicated by the arrow Z, which has been calculated by the compression plate position calculator 86.

After confirming that the phantom 120 is held again, the radiation source drive controller 82 energizes the radiation source 26 to perform a second radiographic image capturing process on the phantom 120. In the second radiographic image capturing process, the radiation source 26 applies radiation 24c to the phantom 120 from the position C (see FIG. 11B). The radiation 24c then passes through the phantom 120 and is detected by the solid-state detector 30 in the image capturing base 32, as radiation representing a radiographic image of the phantom 120. In step S7, the detector controller 88 controls the solid-state detector 30 to acquire the radiographic image from the detected radiation, and to store the acquired radiographic image in the image information storage section 90. After completion of the second radiographic image capturing process, the compression plate drive controller 84 moves the compression plate 34 upwardly to release the phantom 120 from the compression plate 34 and the image capturing base 32.

In step S8, the CAD processor 92 (see FIG. 4) performs image processing sequences such as contrast enhancement and edge enhancement on the two radiographic images stored in the image information storage section 90, thereby generating two radiographic images that exhibit a high contrast ratio between the images 152, 162 and the images 168, 170 (see FIGS. 13A and 13B). Then, the CAD processor 92 outputs the radiographic images to the aspiration space calculator 94 and displays the radiographic images on the display unit 68 and/or the display control panel 42. In step S8, the CAD processor 92 may initially display the two radiographic images, which have not yet been processed, on the display unit 68 and/or the display control panel 42, and thereafter may display the two processed radiographic images on the display unit 68 and/or the display control panel 42.

In step S9, the aspiration space calculator 94 measures lengths x1, y1, y2, z1 of the cavity 144 in the directions indicated by the arrows X, Y, Z in the images 168, 170, and inversely calculates ranges (first spatial range) in the directions indicated by the arrows X, Y, Z of the actual cavity 144 depending on the measured lengths. In step S10, the aspiration space calculator 94 stores the inversely calculated first spatial range and the radiographic images used to calculate the first spatial range in the phantom aspiration range storage section 96. Alternatively, as described above, the aspiration space calculator 94 may determine an average y of the lengths y1, y2 and determine the range of the actual cavity 144 in the directions indicated by the arrow Y from the average y.

In step S11, the aspiration space calculator 94 reads radiographic images from the phantom aspiration range storage section 96, and also reads image data representing the extraction ranges of the biopsy needle 62 from the corrective data storage section 100. Then, the aspiration space calculator 94 identifies the location of the cavity 144 from a difference in contrast between the images 152, 162 and the cavities 144, in the images 168, 170 contained within the read radiographic images. The aspiration space calculator 94 determines a second spatial range of the breast 22, i.e., corrects the extraction ranges into a second spatial range, based on a comparison between the identified location of the cavity 144 and the image data representing the extraction ranges. In step S12, the aspiration space calculator 94 stores the determined second spatial range of the breast 22 in the aspiratable range storage section 98.

Alternatively, the aspiration space calculator 94 may read from the phantom aspiration range storage section 96 a range in the directions indicated by the arrows X, Y, Z of the cavity 144 representative of the first spatial range, and may also read the moduli of elasticity from the corrective data storage section 100. In this case, by multiplying the range in the directions indicated by the arrows X, Y, Z of the cavity 144 by a corrective coefficient based on the moduli of elasticity, the aspiration space calculator 94 can determine a range in the directions indicated by the arrows X, Y, Z representing the second spatial range in the breast 22, i.e., correct the range into a range in the directions indicated by the arrows X, Y, Z representing the second spatial range in the breast 22. In step S12, the aspiration space calculator 94 stores the determined range in the directions indicated by the arrows X, Y, Z in the aspiratable range storage section 98.

In steps S8 through S12, a first spatial range may be measured based on a three-dimensional radiographic image of the phantom 120, which is generated by the CAD processor 92, rather than the two-dimensional images 152, 162, 168, 170. Also, a second spatial range may be determined using the measured first spatial range, and the determined second spatial range may be corrected.

A biopsy procedure using the biopsy apparatus 10 and the mammographic system 12 will be described below with reference to FIG. 16.

Figure 16:
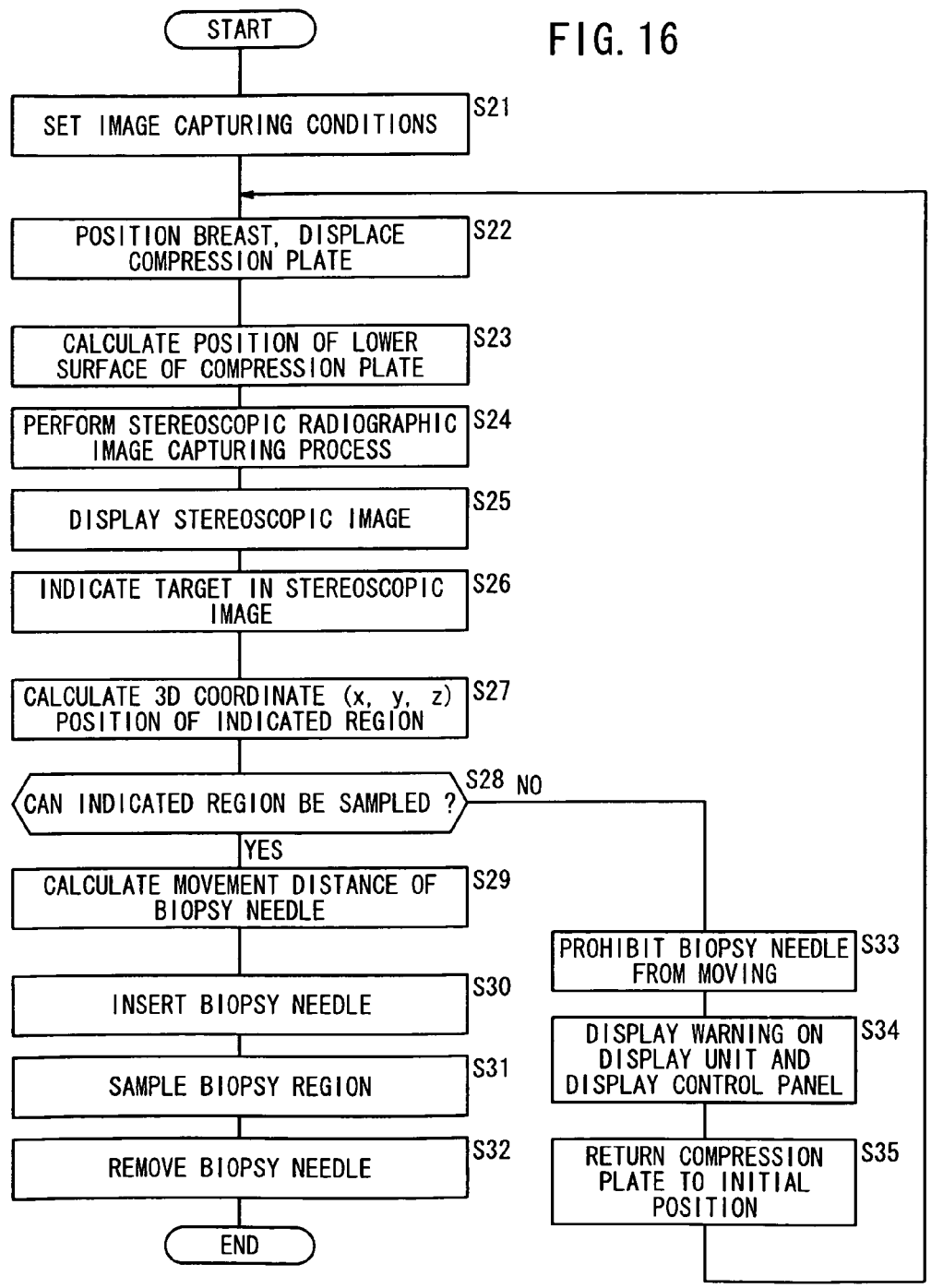
FIG. 16 is a flowchart of a sequence for sampling tissue from a biopsy region using the biopsy apparatus and the mammographic system shown in FIGS. 1, 2 and 4.

As shown in FIG. 16, in step S21, the doctor establishes image capturing conditions depending on the breast 22 using the image capturing condition setting section 80 (see FIG. 4). The established image capturing conditions are set in the radiation source drive controller 82.

In step S22, the doctor positions the breast 22 of the examinee 20. More specifically, the doctor places the breast 22 in a given position, which faces toward the opening 54, on the image capturing base 32, and then operates the compression plate drive controller 84 to move the compression plate 34 toward the image capturing base 32 in the direction indicated by the arrow Z, whereby the compression plate 34 positions the breast 22. The breast 22 is compressed and held in position by the image capturing base 32 and the compression plate 34.

At this time, in step S23, the compression plate position calculator 86 calculates the position of the lower surface of the compression plate 34 with respect to the origin O (see FIG. 3) in the directions indicated by the arrow Z. More specifically, the compression plate position calculator 86 adds the displacement distance detected by the displacement distance detector 50 to the initial positional data of the compression plate 34 (L2+d).

In step S24, the radiation source drive controller 82 energizes the radiation source 26 to perform a stereoscopic radiographic image capturing process on the breast 22. More specifically, the radiation source drive controller 82 angularly moves the radiation source 26 about the hinge 44 selectively to the positions A and B. The radiation source 26 emits radiation 24a, 24b respectively toward the breast 22 from the positions A, B. The radiation 24a, 24b then passes through the breast 22 and is detected by the solid-state detector 30 in the image capturing base 32 as radiation representing respective radiographic images of the breast 22. The detector controller 88 controls the solid-state detector 30 in order to acquire radiographic images from the detected radiation, and to store the acquired radiographic images in the image information storage section 90.

In step S25, the CAD processor 92 performs image processing sequences on the two radiographic images stored in the image information storage section 90, thereby generating two respective radiographic images. Then, the CAD processor 92 displays a stereoscopic image based on the processed radiographic images on the display unit 68 and/or the display control panel 42.

In step S26, while viewing the displayed stereoscopic image and by operating the indicating unit 70, which is a pointing device such as a mouse or the like, the doctor indicates a lesion (target, biopsy region 36) the tissue of which is to be extracted, from among a plurality of lesions in the stereoscopic image.

In step S25, the CAD processor 92 may generate a three-dimensional radiographic image from the two respective two-dimensional images of the breast 22, which are stored in the image information storage section 90, and may display the generated three-dimensional radiographic image on the display unit 68 and/or the display control panel 42. In this case, in step S26, by operating the indicating unit 70 and while viewing the displayed three-dimensional radiographic image, the doctor may indicate a lesion the tissue of which is to be extracted, from among a plurality of lesions in the three-dimensional radiographic image.

In step S27, the target position calculator 104 calculates the three-dimensional coordinate position of the lesion indicated in the stereoscopic image, and outputs information concerning the calculated three-dimensional coordinate position to the decision section 108 and the biopsy needle movement distance calculator 110. The biopsy needle position calculator 106 calculates the three-dimensional coordinate position of the biopsy needle 62, which is displayed in the stereoscopic image, and outputs information concerning the calculated three-dimensional coordinate position to the decision section 108 and the biopsy needle movement distance calculator 110.

The aspiration space calculator 94 reads the changing factor data from the changing factor data storage section 102, and also reads the second spatial range from the aspiratable range storage section 98. The aspiration space calculator 94 then corrects the second spatial range based on the changing factor data, and outputs the corrected second spatial range and the changing factor data to the decision section 108. Alternatively, the aspiration space calculator 94 does not correct the second spatial range, and outputs to the decision section 108 the second spatial range, which has not been corrected, and the changing factor data corresponding to the second spatial range.

In step S28, the decision section 108 determines whether or not the biopsy needle 62 is capable of sampling tissue from the biopsy region 36, based on the changing factor data, the second spatial range, the target coordinate position, the three-dimensional coordinate position of the biopsy needle 62, the position of the lower surface of the compression plate 34 in the directions indicated by the arrow Z, and the positional data of the opening 54.

More specifically, based on the changing factor data, the decision section 108 compares the second spatial range determined by the aspiration space calculator 94 with a threshold value, in order to determine whether or not the second spatial range is greater than the threshold value. The decision section 108 also determines whether or not the biopsy region 36 falls within the extractable range 172 (see FIGS. 14A and 14B). If the biopsy region 36 falls within the extractable range 172, as shown in FIG. 14A, then the decision section 108 also determines whether or not the biopsy needle 62 is capable of sampling tissue from the biopsy region 36 within the aspiration range 174 (second spatial range) of the sampler 64.

If the results of the above three decision processes performed by the decision section 108 are affirmative, i.e., if the results indicate that the biopsy needle 62 is capable of sampling tissue from the biopsy region 36 (step S28: YES), then the decision section 108 displays the affirmative results on the display unit 68 and/or the display control panel 42 in order to let the doctor know the affirmative results, and the decision section 108 indicates to the biopsy needle movement distance calculator 110 that permission has been granted to calculate the distance that the biopsy needle 62 moves and to output the calculated distance to the display unit 68 and/or the display control panel 42.

In step S29, in a case where the biopsy needle movement distance calculator 110 receives from the decision section 108 information concerning permission to calculate the distance that the biopsy needle 62 moves, along with permission to output the calculated distance to the display unit 68 and/or the display control panel 42, the biopsy needle movement distance calculator 110 calculates the distance that the biopsy needle 62 moves with respect to the biopsy region 36, based on the target coordinate position, the three-dimensional coordinate position of the biopsy needle 62, the position of the lower surface of the compression plate 34 in the directions indicated by the arrow Z, and the positional data of the opening 54. Then, the biopsy needle movement distance calculator 110 outputs the calculated distance to the biopsy needle drive controller 112 and the display unit 68 and/or the display control panel 42. Therefore, the display unit 68 and/or the display control panel 42 are capable of displaying the affirmative decision and also the distance over which the biopsy needle 62 is moved.

In step S30, the biopsy needle drive controller 112 controls the biopsy hand assembly 38 based on the distance that the biopsy needle 62 moves, thereby inserting the biopsy needle 62 into the breast 22. More specifically, the biopsy needle drive controller 112 controls the biopsy hand assembly 38 to move the first arm 58 and the second arm 60 of the biopsy hand assembly 38 in the X-Y plane, to thereby position the biopsy needle 62 at a position facing the target (biopsy region 36), i.e., a position facing toward the biopsy region 36 along the directions indicated by the arrow Z, after which the biopsy needle drive controller 112 moves the biopsy needle 62 toward the image capturing base 32. At this time, the biopsy needle 62 is inserted into the breast 22 in order to position the sampler 64 in the vicinity of a tissue of the biopsy region 36, which thus is included within the extraction range (second spatial range) of the sampler 64.

In step S31, while tissue of the biopsy region 36 is included within the second spatial range, the vacuum device 116 starts an aspirating action to cause the sampler 64 of the biopsy needle 62 to start a process of aspirating tissue of the biopsy region 36, thereby aspirating tissue from the biopsy region 36.

In step S32, the biopsy needle 62, which has extracted tissue, is moved toward the compression plate 34, and as a result, the biopsy needle 62 is removed from the breast 22. Thereafter, the compression plate drive controller 84 moves the compression plate 34 upwardly to release the breast 22, whereupon the biopsy procedure is completed.

If the result of one of the three decision processes is negative, e.g., if the second spatial range is smaller than the threshold value, or if the biopsy needle 36 is unable to aspirate tissue of the biopsy region 36 within the present aspiration range 174 even though the biopsy region 36 falls within the extractable range 172 (step S28: NO), then in step S34, the decision section 108 indicates to the biopsy needle movement distance calculator 110 that it is prohibited from calculating the distance that the biopsy needle 62 moves, and outputs the negative result to the display unit 68 and/or the display control panel 42 in order to warn the doctor.

The decision section 108 also sends the negative result to the compression plate drive controller 84, which then returns the compression plate 34 to its initial position in step S35, thereby releasing the breast 22. If the breast 22 were to remain compressed by the compression plate 34, even though the biopsy procedure is prohibited in steps S33 and S34, then the doctor could possibly make a mistake and start to carry out a biopsy procedure on the breast 22, or the examinee 20 could suffer from an increased physical burden.

After step S35, control returns to step S22. After having solved the problem that led to the negative result, e.g., if the second spatial range is smaller than the threshold value, then after the biopsy needle 62 has been replaced with another biopsy needle 62 having a second spatial range greater than the threshold value, step S22 is executed again in order to position the breast 22, and thereafter, the mammographic system 12 performs the biopsy procedure again.

Advantages of the Present Embodiment:

As described above, with the biopsy apparatus 10, the console 40 as the spatial range measuring apparatus, and the spatial range measuring method according to the present embodiment, the biopsy needle 62 is inserted into the phantom 120, which simulates the breast 22, and extracts a portion of the phantom 120. After the portion of the phantom 120 has been extracted, a radiographic image of the phantom 120 is acquired, and a spatial range (second spatial range) is measured within which the biopsy needle 62 can sample tissue of the biopsy region 36 based on the acquired radiographic image.

Since the second spatial range within which the biopsy needle 62 can sample tissue of the biopsy region 36 in the breast 22 is measured based on the radiographic image of the phantom 120 after the portion thereof has been extracted, it is possible to measure, in advance, the second spatial range within which the biopsy needle 62 can sample tissue of the biopsy region 36 prior to the biopsy needle 62 being inserted into the breast 22.

Accordingly, the doctor can avoid inserting the biopsy needle 62 into the breast 22 at a location spaced from the biopsy region 36. Even if the second spatial range changes due to factors such as the properties of the biopsy needle 62, the biopsy procedure is performed according to the measured second spatial range, and hence the biopsy procedure is prevented from failing due to changes in the second spatial range.

Since the phantom 120 and the breast 22 have different properties, the spatial range (first spatial range) within which the phantom 120 can be sampled by the biopsy needle 62 and the spatial range (second spatial range) within which the breast 22 can be sampled by the biopsy needle 62 may differ from each other.

The aspiration space calculator 94 measures the first spatial range, which is formed in the phantom 120, by sampling a portion of the phantom 120, and based on the radiographic image of the phantom 120, corrects the measured first spatial range into the second spatial range within which the biopsy needle 62 can sample tissue of the biopsy region 36.

As the aspiration space calculator 94 determines the second spatial range within which the biopsy needle 62 can sample tissue of the biopsy region 36 in an actual biopsy procedure, the doctor can reliably extract tissue of the biopsy region 36 by inserting the biopsy needle 62 into the breast 22 in order to place the biopsy region 36 within the second spatial range.

The aspiration space calculator 94 can determine the second spatial range accurately by correcting the first spatial range into the second spatial range, using corrective data based on properties of the phantom 120 and properties of the breast 22.

The aspiration space calculator 94 may calculate the second spatial range when the radiographic image of the phantom 120 is acquired, or immediately before a biopsy procedure is carried out. In order to enable the aspiration space calculator 94 to calculate the second spatial range, the biopsy apparatus 10 includes the phantom aspiration range storage section 96, which stores therein the first spatial range measured by the aspiration space calculator 94, the corrective data storage section 100, which stores corrective data, and the aspiratable range storage section 98, which stores therein the second spatial range corrected by the aspiration space calculator 94. It is thus possible for the aspiration space calculator 94 to measure the first spatial range, and to correct the first spatial range into the second spatial range at a suitable time, immediately after the radiographic image of the phantom 120 is acquired or immediately before the doctor performs a biopsy procedure.

The second spatial range may possibly be changed due to factors such as the properties of the biopsy needle 62. If the doctor operates the indicating unit 70 to indicate the biopsy region 36 and the target position calculator 104 calculates the position of the biopsy region 36, then the decision section 108 determines whether or not the biopsy needle 62 is capable of sampling tissue from the biopsy region 36 based on the position of the biopsy region 36, the second spatial range, and the changing factor data. Inasmuch as the decision section 108 determines whether or not the biopsy needle 62 is capable of sampling tissue from the biopsy region 36 in view of changing factors of the second spatial range, if the result is affirmative, thereby indicating that the biopsy needle 62 is capable of sampling tissue from the biopsy region 36, then a biopsy procedure can be performed. On the other hand, if the result is negative, thereby indicating that the biopsy needle 62 is incapable of sampling tissue from the biopsy region 36, then the biopsy needle 62 can be prevented from being erroneously inserted into the breast 22.

If the result is displayed on the display unit 68 and/or the display control panel 42 to thereby inform the doctor of the result, then the doctor can easily recognize whether a biopsy procedure should be carried out or not.

If the decision section 108 judges that the biopsy needle 62 is capable of sampling tissue from the biopsy region 36, then the decision section 108 displays the result on the display unit 68 and/or the display control panel 42 to inform the doctor of the result, and permits the biopsy needle movement distance calculator 110 to calculate the distance that the biopsy needle 62 moves. The decision section 108 also permits the display unit 68 and/or the display control panel 42 to display the calculated distance. If the decision section 108 judges that the biopsy needle 62 is incapable of sampling tissue from the biopsy region 36, then the decision section 108 displays the fact that sampling of tissue is prohibited on the display unit 68 and/or the display control panel 42 to thereby warn the doctor, and the decision section 108 prohibits the biopsy needle movement distance calculator 110 from calculating the distance that the biopsy needle 62 moves.

If the decision section 108 makes an affirmative decision indicating that the biopsy needle 62 is capable of sampling tissue from the biopsy region 36, then since the affirmative decision and the distance that the biopsy needle 62 moves are displayed on the display unit 68 and/or the display control panel 42 to let the doctor know of the affirmative decision and the distance, the doctor can accurately and reliably perform a biopsy procedure according to the affirmative decision and the distance, which are displayed. Since the biopsy needle movement distance calculator 110 calculates the distance that the biopsy needle 62 moves according to the affirmative result, if the biopsy needle 62 is moved by the calculated distance, then tissue of the biopsy region 36, which is indicated by the indicating unit 70, reliably falls within the second spatial range. As a result, tissue of the biopsy region 36 can efficiently be extracted.

If the decision section 108 makes a negative decision indicating that the biopsy needle 62 is incapable of sampling tissue from the biopsy region 36, then since only the negative decision is displayed on the display unit 68 and/or the display control panel 42 to let the doctor know of the negative decision, the doctor can easily recognize that the biopsy procedure cannot be performed.

In a case where the second spatial range is changed (reduced) due to factors such as the properties of the biopsy needle 62, the tissue of the biopsy region 36 may fall outside of the second spatial range, or may not be extracted, even if the biopsy needle 62 is accurately inserted into the breast 22.

Accordingly, if the second spatial range is smaller than the threshold value, then the decision section 108 may judge that the biopsy needle 62 is unable to sample tissue of the biopsy region 36. The biopsy procedure thus is reliably canceled if there is any possibility that the biopsy procedure will fail due to a change in the second spatial range.

In the case that the extractable range 172 within which the biopsy needle 62 can extract a tissue of the biopsy region 36 is preset, the decision section 108 may judge that the biopsy needle 62 is incapable of sampling tissue from the biopsy region 36 if the position of the biopsy region 36 falls outside of the extractable range 172. Since there is a possibility that the biopsy procedure will fail if the position of the biopsy region 36 falls outside of the extractable range 172, the biopsy procedure is reliably canceled by making the foregoing decision.

If the decision section 108 permits the biopsy needle movement distance calculator 110 to calculate the distance that the biopsy needle 62 moves, then the biopsy needle movement distance calculator 110 calculates the distance that the biopsy needle 62 moves and outputs the calculated distance to the biopsy needle drive controller 112. The biopsy needle drive controller 112 then inserts the biopsy needle 62 into the breast 22 based on the distance input thereto. The biopsy apparatus 10 then moves the biopsy needle 62 based on the input distance, thereby automatically performing a biopsy procedure on the breast 22. As a result, the burden posed on the doctor by the biopsy procedure is reduced.

The biopsy needle 62 includes the sampler 64 for aspirating and sampling tissue of the biopsy region 36, disposed in a side wall of the biopsy needle 62 in the vicinity of the tip end 132 thereof. The sampler 64 is connected through the vacuum hose 114 to the vacuum device 116, which performs an aspirating action on the tissue of the biopsy region 36 or a portion of the phantom 120. If the changing factor data refer to data representative of characteristics of the biopsy needle 62, including the sampler 64, characteristics of the vacuum hose 114, and characteristics of the vacuum device 116, then the decision section 108 can determine more accurately whether or not the biopsy needle 62 is capable of sampling tissue from the biopsy region 36.

If the biopsy region 36 is spaced from the sampler 64 along the direction in which the biopsy needle 62 is inserted into the breast 22, then moving the biopsy needle 62 along that direction in order to displace the sampler 64 toward the position of the biopsy region 36 brings the tissue of the biopsy region 36 into the second spatial range, thereby making it possible to extract tissue from the biopsy region 36. If the biopsy region 36 is spaced from the sampler 64 along the direction in which the biopsy needle 62 is inserted into the breast 22 and yet falls outside of the second spatial range, then it is difficult to move the biopsy needle 62 radially in order to bring the biopsy region 36 into the second spatial range. In such a case, it is necessary to pull out the biopsy needle 62 from the breast 22 and reinsert the biopsy needle 62 into the breast 22.

To avoid such a difficulty, it is preferable for the radiation source 26 to apply radiation 24 along the direction in which the biopsy needle 62 is inserted into the phantom 120, and for the solid-state detector 30 to convert the radiation 24 that has passed through the phantom 120 into a radiographic image on a projection plane which is substantially perpendicular to the direction in which the biopsy needle 62 is inserted into the phantom 120. In this manner, the radiographic image becomes an image on a plane (projection plane) along a radial direction of the biopsy needle 62, i.e., along a direction perpendicular to the direction in which the biopsy needle 62 is inserted into the phantom 120. By determining the width of the second spatial range along the radial direction, it is possible to determine easily whether or not the biopsy region 36 falls within the second spatial range before the biopsy procedure actually is performed.

It has been described above that, in the first radiographic image capturing process, radiation 24 (24c) is applied along a direction in which the biopsy needle 62 is inserted in order to acquire a radiographic image, and thereafter, in the second radiographic image capturing process, radiation 24 (24c) is applied along a direction which is substantially perpendicular to the direction in which the biopsy needle 62 is inserted in order to acquire a radiographic image. However, the present embodiment is not limited to such a sequence, and it is preferable to determine the first spatial range and the second spatial range (ranges in directions indicated by the arrows X and Y) based on a radiographic image acquired in at least the first radiographic image capturing process.

More specifically, since the aspiration range in the directions indicated by the arrow Z (the length in the directions indicated by the arrow Z) of the opening 136, which acts as the sampler 64, is wider than the aspiration ranges in the directions indicated by the arrows X and Y (lengths in the directions indicated by the arrows X and Y), the first spatial range and the second spatial range (ranges in the directions indicated by the arrows X and Y) may be determined based only on a radiographic image acquired in the first radiographic image capturing process, and a preset prescribed value (given value) may be substituted for the range in the directions indicated by the arrow Z.

In addition, as shown in FIGS. 8A through 13B, the opening 136 is defined as the sampler 64 in the side wall of the biopsy needle 62, and a portion of the phantom 120 or tissue of the biopsy region 36, which faces the opening radially of the biopsy needle 62, is extracted through the opening 136. Therefore, information about the radial directions of the biopsy needle 62, i.e., the directions indicated by the arrows X and Y, serves more importantly as information concerning the first spatial range and the second spatial range than information about the direction in which the biopsy needle 62 is inserted, i.e., directions indicated by the arrow Z. According to the present embodiment, it is preferable to determine the first spatial range and the second spatial range using the radiographic image acquired in at least the first radiographic image capturing process, which contains therein at least positional information in the directions indicated by the arrows X and Y.

In the present embodiment, measurements of the first spatial range and the second spatial range at the time the biopsy needle 62 is inserted once into the phantom 120 have been described. However, it also is possible to measure the first spatial range and the second spatial range by inserting the biopsy needle 62 into the phantom 120 at the same position a plurality of times in order to extract a portion of the phantom 120. In this case, if the second spatial range obtained in a case where the biopsy needle 62 is inserted into the phantom 120 once is stored in the aspiratable range storage section 98 along with second spatial ranges obtained in a case where the biopsy needle 62 is inserted into the phantom 120 a plurality of times, then upon performing the biopsy procedure, the doctor can select a desired second spatial range by operating the display control panel 42.

Moreover, according to the present embodiment, the decision section 108 performs decision-making processes in a case where the biopsy procedure is performed. However, the decision section 108 may also perform decision processes in a case where the biopsy apparatus 10 starts to operate each morning. If the decision section 108 performs decision processes each time that a biopsy procedure is performed or each morning, the biopsy apparatus 10 keeps a desired level of quality control (QC). Furthermore, to achieve a higher level of quality control, the first spatial range and the second spatial range may be measured using the phantom 120 each morning or each time that the biopsy apparatus 10 has been operated a predetermined number of times.

In the present embodiment, the phantom 120 includes the first member 122, which simulates the breast 22, and the second members 124 disposed in the first member 122, each of which simulate tissue of the biopsy region 36. The first member 122 is made of a material that is permeable to radiation 24, whereas the second members 124 are made of a material that is less permeable to radiation 24 than the first member 122, or which is impermeable to radiation 24.

Since the second members 124, which simulate tissue of the biopsy region 36, are disposed in the first member 122, it is possible to train the doctor to perform a biopsy procedure for sampling the tissue. The doctor is trained to perform a biopsy procedure using the phantom, and as a result, the doctor becomes more skillful at performing the biopsy procedure in order to sample calcified tissue in the breast 22. Since the second members 124 are less permeable to radiation 24 than the first member 122, or are impermeable to radiation 24, in a case where a radiographic image capturing process is performed on the phantom 120 in order to acquire a radiographic image thereof, it is possible to easily distinguish the first member 122 and the second members 124 from each other. By measuring a spatial range within which the biopsy needle 62 can extract tissue of the biopsy region 36 based on an image of the phantom 120, the aforementioned advantages of the biopsy apparatus 10, the console 40, and the spatial range measuring method can easily be achieved.

If second members 124 in the form of particles are disposed substantially uniformly throughout the first member 122, it is possible to train the doctor to position the biopsy needle 62 accurately in tissue of the biopsy region 36.

According to the present embodiment, if a plurality of first spatial ranges are formed in the phantom 120, as shown in FIGS. 17A through 18C, then the first spatial ranges can be measured, and second spatial ranges can be identified from the measured first spatial ranges.

Figure 17B:
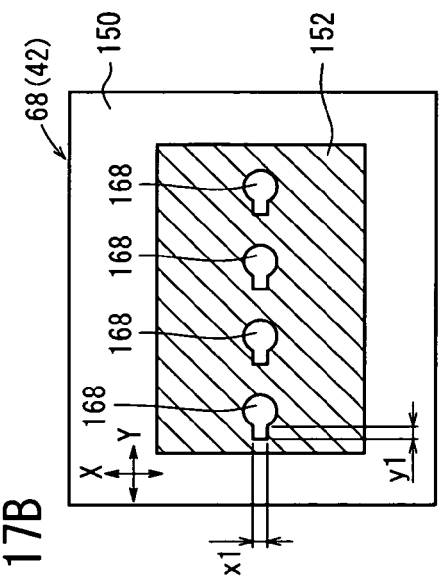
FIGS. 17B and 17C are views showing radiographic images produced from the radiographic image capturing process shown in FIG. 17A.
Figure 17C:
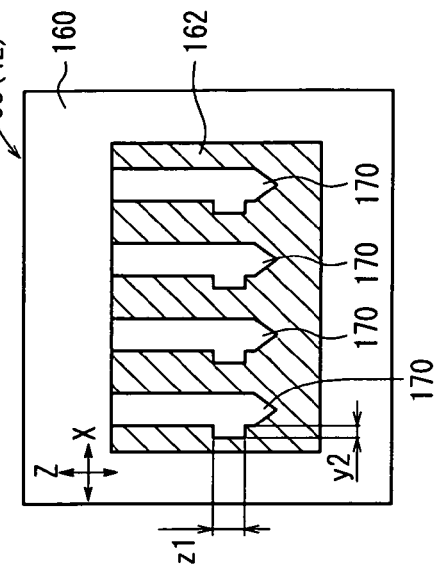
Figure 17A:
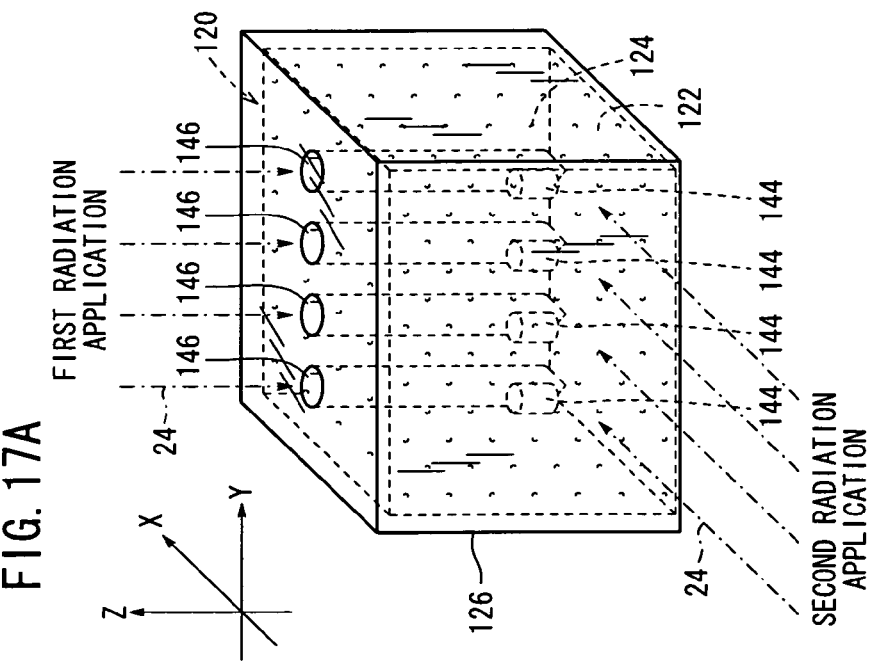
FIG. 17A is a perspective view illustrative of a radiographic image capturing process performed on a phantom, which has a plurality of cavities and passages through which the biopsy needle has been pulled out.

In FIG. 17A, an array of cavities 144 and passages 146, which are spaced at intervals along directions indicated by the arrow Y, are disposed in the phantom 120. The directions indicated by the arrow Y refer to directions toward and away from the breast 22 of the examinee 20 (see FIGS. 1 and 2). FIG. 17B shows a radiographic image captured of the phantom 120 shown in FIG. 17A by a first radiographic image capturing process. In the radiographic image shown in FIG. 17B, images 168 representing the cavities 144 and the passages 146 are displayed or arranged in an array along directions indicated by the arrow Y. FIG. 17C shows a radiographic image in side elevation captured of the phantom 120 shown in FIG. 17A by a second radiographic image capturing process. In the radiographic image shown in FIG. 17C, images 170 representing the cavities 144 and the passages 146 are displayed or arranged so as not to overlap each other.

Figure 18B:
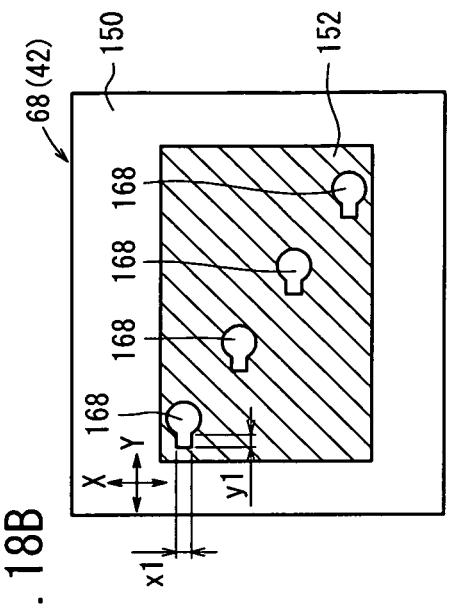
FIGS. 18B and 18C are views showing radiographic images produced from the radiographic image capturing process shown in FIG. 18A.
Figure 18C:
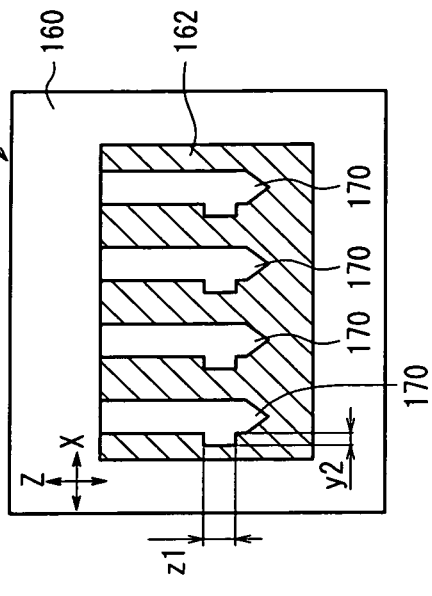
Figure 18A:
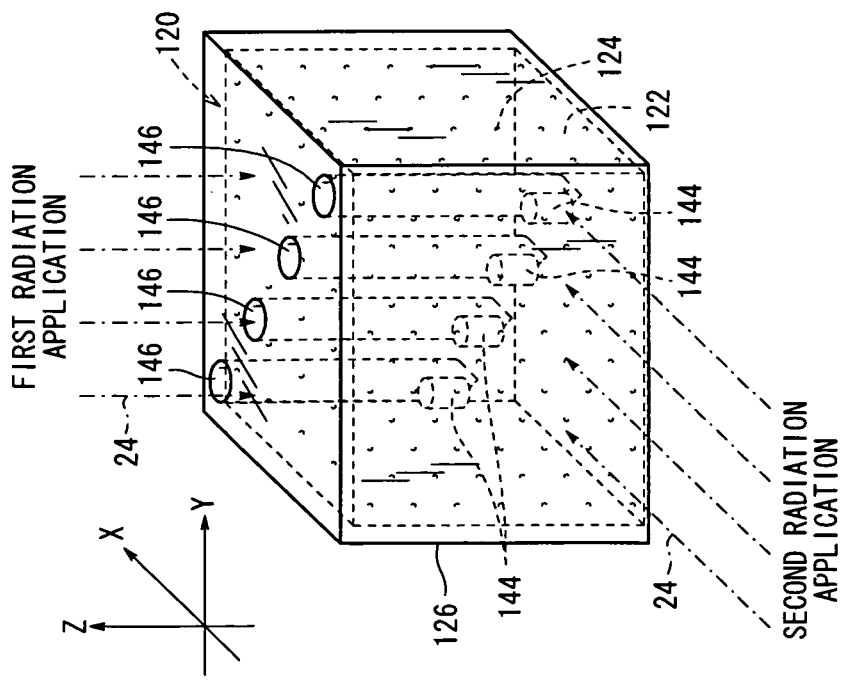
FIG. 18A is a perspective view illustrative of another radiographic image capturing process performed on a phantom, which has a plurality of cavities and passages through which the biopsy needle has been pulled out.

In FIG. 18A, an array of cavities 144 and passages 146, which are spaced at given intervals, are disposed along the X-Y plane in the phantom 120, in a direction oblique to the directions indicated by the arrows X and Y. FIG. 18B shows a radiographic image captured of the phantom 120 shown in FIG. 18A by a first radiographic image capturing process. In the radiographic image shown in FIG. 18B, images 168 representing the cavities 144 and the passages 146 are displayed or arranged in an array along the X-Y plane in an oblique direction. FIG. 18C shows a radiographic image in side elevation captured of the phantom 120 shown in FIG. 18A by a second radiographic image capturing process. In the radiographic image shown in FIG. 18C, images 170 representing the cavities 144 and the passages 146 are displayed or arranged so as not overlap each other.

With the cavities 144 and the passages 146 being formed as sampling spaces in the phantom 120, it is easy to determine second spatial ranges at positions in the breast 22 that correspond to the cavities 144 and the passages 146. If a plurality of biopsy needles 62 having different characteristics are inserted into the phantom 120 in order to form a plurality of cavities 144 and passages 146 therein, then the second spatial ranges, which depend on such cavities 144 and passages 146, may possibly differ from each other. In such a case, second spatial ranges depending on the respective biopsy needles 62 may be determined in advance, and in a case where a biopsy procedure is carried out, one of the biopsy needles 62 may be selected depending on the position and size of the biopsy region 36. In this manner, the biopsy procedure can be carried out reliably and efficiently.

Although a certain preferred embodiment of the present invention has been shown and described in detail, it should be understood that various changes and modifications may be made to the embodiment without departing from the scope of the invention as set forth in the appended claims.

What is claimed is:

1. A biopsy apparatus comprising:
   a biopsy needle for insertion into an object to be examined in a living body thereby to sample tissue of a biopsy region in the object; and
   a spatial range measuring section, which measures a spatial range within which the biopsy needle is capable of sampling the tissue of the biopsy region, based on an image of a phantom that simulates the object, the image being captured after the biopsy needle has been inserted into the phantom and a portion of the phantom has been extracted.

2. The biopsy apparatus according to claim 1, wherein the spatial range measuring section measures a first spatial range depending on the portion of the phantom and which is formed in the phantom by extracting the portion of the phantom, based on the image of the phantom, and corrects the measured first spatial range into a second spatial range within which the biopsy needle is capable of sampling the tissue of the biopsy region.

3. The biopsy apparatus according to claim 2, wherein the spatial range measuring section corrects the measured first spatial range into the second spatial range using corrective data based on properties of the phantom and properties of the object.

4. The biopsy apparatus according to claim 3, wherein the corrective data comprise either data based on a spatial range within which the biopsy needle is capable of sampling the portion of the phantom and the spatial range within which the biopsy needle is capable of sampling the tissue of the biopsy region, or data based on characteristic values of a material that makes up the phantom and characteristic values of a material that makes up the object.

5. The biopsy apparatus according to claim 3, further comprising:
   a first spatial range storage section that stores the first spatial range measured by the spatial range measuring section;
   a corrective data storage section that stores the corrective data; and
   a second spatial range storage section that stores the second spatial range corrected by the spatial range measuring section.

6. The biopsy apparatus according to claim 5, further comprising:
   a biopsy region indicator that indicates the biopsy region to be sampled by the biopsy needle;
   a biopsy region position calculator that calculates the position of the biopsy region indicated by the biopsy region indicator;
   a changing factor data storage section that stores changing factor data representative of a changing factor of the second spatial range; and
   a decision section that reads the second spatial range from the second spatial range storage section, reads the changing factor data from the changing factor data storage section, and determines whether the biopsy needle is capable of sampling the tissue of the biopsy region indicated by the biopsy region indicator, based on the position of the biopsy region, the read second spatial range, and the read changing factor data.

7. The biopsy apparatus according to claim 6, further comprising:
   an annunciating section for annunciating a decision made by the decision section.

8. The biopsy apparatus according to claim 7, further comprising:
   a biopsy needle position calculator that calculates the position of the biopsy needle in a case that the biopsy region indicator indicates the biopsy region; and
   a biopsy needle movement distance calculator that calculates a distance that the biopsy needle moves with respect to the biopsy region, based on the position of the biopsy region and the position of the biopsy needle,
   wherein, if the decision section judges that the biopsy needle is capable of sampling the tissue of the biopsy region, the decision section indicates outwardly through the annunciating section that the biopsy needle is capable of sampling the tissue of the biopsy region, and permits the biopsy needle movement distance calculator to calculate the distance that the biopsy needle moves, and also permits the annunciating section to indicate the calculated distance, and
   if the decision section judges that the biopsy needle is incapable of sampling the tissue of the biopsy region, the decision section indicates outwardly through the annunciating section a prohibition of sampling the tissue of the biopsy region by the biopsy needle, and prohibits the biopsy needle movement distance calculator from calculating the distance that the biopsy needle moves.

9. The biopsy apparatus according to claim 8, wherein the decision section judges that the biopsy needle is incapable of sampling the tissue of the biopsy region if the second spatial range is smaller than a threshold value based on the changing factor data.

10. The biopsy apparatus according to claim 8, wherein the decision section judges that the biopsy needle is incapable of sampling the tissue of the biopsy region if the position of the biopsy region falls outside of an insertable range within which the biopsy needle can be inserted into the object.

11. The biopsy apparatus according to claim 8, further comprising a biopsy needle movement controller that controls movement of the biopsy needle,
    wherein, if the decision section permits the biopsy needle movement distance calculator to calculate the distance that the biopsy needle moves, the biopsy needle movement distance calculator calculates the distance that the biopsy needle moves and outputs the calculated distance to the biopsy needle movement controller, and
    wherein the biopsy needle movement controller inserts the biopsy needle into the object based on the distance input thereto.

12. The biopsy apparatus according to claim 6, wherein the biopsy needle has a sampler defined in a side wall near a tip end thereof, for aspirating and extracting the tissue of the biopsy region or the portion of the phantom;
    the sampler is connected through an aspirating passage to an aspirating device for aspirating the tissue of the biopsy region or the portion of the phantom; and
    the changing factor data comprise data representing characteristics of the biopsy needle including the sampler, characteristics of the aspirating passage, and characteristics of the aspirating device.

13. The biopsy apparatus according to claim 1, wherein the image of the phantom is captured by applying radiation from a radiation source to the phantom after the portion of the phantom has been extracted, and converting the radiation that has passed through the phantom into a radiographic image with a radiation detector.

14. The biopsy apparatus according to claim 13, wherein the biopsy needle has a sampler defined in a side wall near a tip end thereof, for aspirating and extracting the tissue of the biopsy region or the portion of the phantom;

the radiation source applies the radiation at least along a direction in which the biopsy needle is inserted into the phantom; and the radiation detector converts the radiation that has passed through the phantom into a radiographic image on a projection plane of the radiation, which is substantially perpendicular to the direction in which the biopsy needle is inserted into the phantom.

15. The biopsy apparatus according to claim 14, wherein the biopsy needle is inserted into the phantom a plurality of times for extracting respective portions of the phantom, thereby forming a plurality of sampling spaces in the phantom depending on the portions of the phantom; and the sampling spaces are formed so as not to overlap each other in side elevation.

16. The biopsy apparatus according to claim 15, wherein the phantom simulates a breast of a human body; and the biopsy needle is inserted into the phantom a plurality of times in spaced relation to a chest wall of the human body, thereby forming the sampling spaces in the phantom.

17. A spatial range measuring apparatus comprising a spatial range measuring section for measuring a spatial range within which a biopsy needle is capable of sampling tissue of a biopsy region in an object to be examined in a living body, based on an image of a phantom that simulates the object, the image being captured after the biopsy needle has been inserted into the phantom and a portion of the phantom has been extracted.

18. A spatial range measuring method comprising:

inserting a biopsy needle into a phantom that simulates an object to be examined in a living body, and extracting a portion of the phantom;

acquiring an image of the phantom after the portion of the phantom has been extracted; and measuring a spatial range within which the biopsy needle is capable of sampling tissue of a biopsy region in the object, based on the image of the phantom.

\* \* \* \* \*